US005744460A

United States Patent [19]
Müller et al.

[11] Patent Number: 5,744,460
[45] Date of Patent: Apr. 28, 1998

[54] COMBINATION FOR TREATMENT OF PROLIFERATIVE DISEASES

[75] Inventors: Marcel Müller, Allschwil, Switzerland; Thomas Geiger, Freiburg, Germany; Karl-Heinz Altmann, Reinach, Switzerland; Doriano Fabbro, Arlesheim, Switzerland; Nicholas M. Dean, Encinitas, Calif.; Brett Monia, Carlsbad, Calif.; Clarence Frank Bennett, Carlsbad, Calif.

[73] Assignee: Novartis Corporation, Summit, N.J.

[21] Appl. No.: 612,775

[22] Filed: Mar. 7, 1996

[51] Int. Cl.$^6$ .................. A61K 31/44; A61K 31/53; A61K 31/70; A61K 31/445; A61K 31/505; A61K 48/00; C07H 21/04

[52] U.S. Cl. ............... 514/44; 514/34; 514/242; 514/274; 514/283; 514/322; 536/24.5

[58] Field of Search ............... 514/44, 283, 34, 514/242, 274, 322; 536/24.5

[56] References Cited

U.S. PATENT DOCUMENTS

| | | | |
|---|---|---|---|
| 5,387,676 | 2/1995 | Zavada et al. | 536/23.5 |
| 5,457,191 | 10/1995 | Cook et al. | 536/27.13 |
| 5,525,490 | 6/1996 | Erickson et al. | 435/29 |
| 5,539,094 | 7/1996 | Reed et al. | 536/23.5 |
| 5,550,019 | 8/1996 | Reed | 435/6 |
| 5,585,479 | 12/1996 | Hoke et al. | 536/24.5 |

FOREIGN PATENT DOCUMENTS

| | | |
|---|---|---|
| 0359981 | 3/1990 | European Pat. Off. |
| 9104753 | 4/1991 | WIPO |
| 9319203 | 9/1993 | WIPO |
| 9320101 | 10/1993 | WIPO |
| 9408625 | 4/1994 | WIPO |
| 9415645 | 7/1994 | WIPO |
| 9423755 | 10/1994 | WIPO |
| 9429455 | 12/1994 | WIPO |
| 95/02069 | 1/1995 | WIPO |
| 9501369 | 1/1995 | WIPO |
| 9502069 | 1/1995 | WIPO |
| WO 95/02069 | 1/1995 | WIPO |
| 9503833 | 2/1995 | WIPO |
| 9506659 | 3/1995 | WIPO |
| 9508350 | 3/1995 | WIPO |
| 9514707 | 6/1995 | WIPO |
| 9520044 | 7/1995 | WIPO |
| 9532987 | 12/1995 | WIPO |
| 9605298 | 2/1996 | WIPO |
| 96/19240 | 6/1996 | WIPO |
| 9622101 | 7/1996 | WIPO |
| 96/39154 | 12/1996 | WIPO |

OTHER PUBLICATIONS

G. K. Schwartz, et al., J. Natl. Cancer Inst., vol. 87, No. 18, 1995, pp. 1394–1399.

Uhlmann E, et al. "Antisense oligonucleotides: A new therapeutic principle." Chem. Rev. 90: 543–584, 1990.

Skorski T, et al. "Highly efficient elimination of Philadelphia leukemic cells by exposure to bcr/abl antisense oligonucleotides combined with mafosfamide." J. Clin. Invest. 92: 194–202, 1993.

Malgorzata N–S. "Oncogene–targeted antisense oligodeoxynucleotides combined with chemotherapy or immunotherapy: A new approach for tumor treatment." Folia Histochemica et Cytobiologica 32: 35–40, 1994.

Monia BP. "Evaluation of 2' modified oligonucleotides containing 2-deoxy gaps as antisense inhibitors of gene expression." JBC 268: 14514–14522, 1993.

Nishizuka Y. "The molecular heterogeneity of protein kinase C and its implications for cellular regulation." Nature 334: 661–665, 1988.

Orkin SH. "Report and Recommendations of the Panel to Assess the NIH Investment in Research on Gene Therapy.", 1995.

Szczylik et al "Selective Inhibition of Leukemia Cell Proliferation by BCR–ABL Antisense Oligodeoxynucleotides" Science vol. 253 (1991) pp. 562–565.

Nieborowska–Skórska! "Oncogene–targeted antisense oligodeoxynucleotides combined with chemotherapy or immunotherapy: A new approach for tumor treatment ?." Folia Histochemica et Cytobiologica, vol. 32, No. 1, 1994 pp. 35–40.

Taroszewski et al "Concerning Antisense Inhibition of the Multiple Drug Resistance Gene" Cancer Communications, vol. 2, No. 8 1990 (pp. 287–294).

Isis Pharmaceuticals Press Release dated Jan. 23, 1996, "Isis Pharmaceuticals Initiates Clinical trials with Novel Antisense Cancer Compound Targeted to PKC–α Inhibition".

(List continued on next page.)

Primary Examiner—Douglas W. Robinson
Assistant Examiner—Amy J. Nelson
Attorney, Agent, or Firm—Henry P. Nowak

[57] ABSTRACT

The invention relates to combinations of PKC-targeted (especially PKC-α-targeted) deoxyribo- and ribo-oligonucleotides and derivatives thereof with other chemotherapeutic compounds, as well as to pharmaceutical preparations and/or therapies, in relation to disease states which respond to such oligonucleotides or oligonucleotide derivatives, especially to to modulation of the activity of a regulatory protein. In particular, the invention relates to products or combinations comprising antisense oligonucleotides or oligonucleotide derivatives targeted to nucleic acids encoding human PKC and other (preferably standard) chemotherapeutics, either in fixed combination or for chronologically staggered or simultaneous administration, and the combined use of both classes of compounds, either in fixed combination or for chronologically staggered or simultaneous administration, for the treatment of proliferative diseases, especially tumor diseases, that can be treated by inhibition of PKC activity, that is, where the antisense oligonucleotides or oligonucleotide derivatives are targeted to nucleic acids encoding the regulatory protein PKC or active mutated derivatives thereof.

12 Claims, No Drawings

OTHER PUBLICATIONS

Calabretta "Inhibition of Protooncogene Expression by Antisense Oligodeoxynucleotides: Biological and Therapeutic Implications" Cancer Research 54, 4505–4510 Sep. 1991.

Skorski et al "Highly Efficient Elimination of Philadelphia Leukemic Cells by Exposure to bcr/abl Antisense Oligodeoxynucleotides Combined with Mafosfamide" J Clinical Invest vol. 92, (1993) 194–202.

Corrias "An Oligomer Complimontary to the 5' End Region of MDRL Gene Decreases Resistance to Doxorubicin of Human Adenocarcinoma–Resistance Cells" Anticancer Research 12, 1431–1438 (1992).

Derwent Abstract 96–354302 [35], 1996.

Chemical Abstract, vol. 37, No. 2807, 511, 1996.

Guleria et al, Nature Medicine 2 (3), 334 (1996).

Mizutani et al, Cancer 74 (9), 2546 (1994).

Milligan et al, J. Med. Chem 36 (14), 1923 (1993).

Clark et al, Cancer Supplement 78 (3), 688 (1996).

Chemical Abstract, vol. 37, No. 240.5, 352, 1996.

Ma et al, Fundam Clin. Pharmacol. 10, 97–115 (1996).

Citti et al, Carcinogenesis 17 (1), 25–29 (1996).

Chemical Abstract, vol. 86, No. 2955, 1, 742a, (1995).

Chemical Abstract, vol. 36, No. 2571, 431 (1995).

Chemical Abstract, vol. 36, No. 2032, 341, (1996).

Chemical Abstract, vol. 36, No. 1704, 287, (1996).

Steele et al, Cancer Research 53, 2330 (1993).

Chemical Abstract, vol. 153, No. 166, 270A, (1995).

Chemical Abstract, vol. 84, No. 2043, 1,514a (1994).

Chemical Abstract, vol. 35, No. 1543, 258, (1994).

Chemical Abstract, vol. 84, No. 552, (1994).

Tortora et al, Biochem. Biophys. Res. Commun. 177 (3), 1133 (1991).

Chemical Abstract, vol. 32, No. 2570, (1991).

Chemical Abstract, vol. 31, No. 221, (1990).

Alama et al., Pharm Res. 22, Suppl. 2,2 (1990).

Dean et al, J. Biol. Chem. 269 (23), 16416–24(1994).

Maier, et al, Experimental Cell Research 205, 52–58 (1993).

The Genesis Report/Rx, Jun. 1993, p. 15.

Ahmad et al, Mol. Pharmacology 43, 858 (1993).

Chemical Abstract, vol. 33, No. 550, 92, (1992).

Chemical Abstract, vol. 57, (2), 1005–B (1996).

Cho–Chung et al, Pharm. Ther. 60, 265–88 (1993).

Roninson: Cancer Biotechnology Weekly Nov. 6, 1995.

Blagosklonny et al, Cancer Researcher Weekly Sep. 26, 1994.

Cho–Chung: Crisp data Base NIH, Publication year 1994 (entered into database Jul. 1995).

Chemical Abstract, vol. 95, 206843, (1994).

Blagosklonny et al, Anti–Cancer Drugs 5, 437–442 (1994).

Baltuch et al, J. Neuro–Oncology 24, 241–50 (1995).

Proc. Amer. Assoc. Cancer Res. vol. 35, p. 617, No. 3680 (1994).

COMBINATION FOR TREATMENT OF PROLIFERATIVE DISEASES

FIELD OF THE INVENTION

This invention relates to combinations of PKC-targeted (especially PKC-α-targeted) deoxyribo- and ribo-oligonucleotides and derivatives thereof with other chemotherapeutic compounds, as well as to pharmaceutical preparations and/or therapies, in relation to disease states which respond to such oligonucleotides or oligonucleotide derivatives, especially to modulation of the activity of a regulatory protein. In particular, the invention relates to products or combinations comprising antisense oligonucleotides or oligonucleotide derivatives targeted to nucleic acids encoding (especially human) PKC and other (preferably standard) chemotherapeutics, either in fixed combination or for chronologically staggered or simultaneous administration, and the combined use of both classes of compounds, either in fixed combination or for chronologically staggered or simultaneous administration, for the treatment of proliferative diseases, especially tumor diseases, that can be treated by inhibition of PKC, especially PKC-α activity, that is, where the antisense oligonucleotides or oligonucleotide derivatives are targeted to nucleic acids encoding the regulatory protein PKC, especially PKC-α, or active mutated derivatives thereof.

BACKGROUND OF THE INVENTION

The extensive information that has been accumulated over the past decade concerning the molecular basis of mammalian cell transformation has led to the unifying concept of growth regulation and its disorders in cancer cells. The fact that many products of "cancer genes" encode for proteins that regulate normal mitogenesis suggests that the carcinogenic process may be viewed as a multistep and progressive disorder of signal transduction. This conceptual framework has provided a basis for the development of novel anticancer strategies and therapeutic modalities. Almost every mitogenic signal is amplified and transduced inside cells by protein kinase (PK) cascades either by receptor activated tyrosine phosphorylation or by receptor coupling to GTP-binding proteins. Most mitogenic pathways utilize unique and/or overlapping parts of these protein kinase cascades. Accordingly mutant alleles of these PK genes or of oncogenes (like ras) that signal through these PKs are able to perturb entire signaling networks leading to the deregulation of cell differentiation, division and/or apoptosis. The anticancer strategy is, consequently, based on the assumption that blocking deregulated mitogenic signal transduction at the level of PKs will cause cancer growth inhibition. This approach is likely to identify compounds with less side effects compared to standard chemotherapeutic agents.

Protein kinase C (PKC) has attracted attention as a target for cancer drug development for a number of reasons. PKC is a primary receptor for the tumor-promoting phorbol esters and PKC levels are altered in many tumor cells. In addition, cells overexpressing PKC are susceptible to transformation by H-ras. Overexpression of several PKC isozymes has been demonstrated to cause transformation of cells. However, most of the available drugs that modulate PKC activity appear to act on all the isoforms and no selective inhibitor of a given subtype has been identified as yet. In addition, these drugs interfering with intracellular signaling are expected to have far less unwanted side effects than the classical chemotherapeutic agents that are currently used. The phosphotioate antisense oligonucleotide that corresponds to the sequence 5'-GTT CTC GCT GGT GAG TTT CA-3' (SEQ-ID NO: 1, referred to as SEQ-ID NO: 1-ODN hereinafter, is a representative of the first class of isozyme-specific inhibitors of PKC-α expression which inhibits the expression of PKC-α mRNA and protein both in vitro and in vivo. SEQ-ID NO: 1-ODN shows potent antitumor activity in nude mice in vivo as a single agent. In addition, additive and even synergistic effects between PKC-α ODNs and standard chemotherapeutic drugs have been observed in nude mouse xenograft models. SEQ-ID NO: 1-ODN might therefore be used both as a single agent and in combination therapy for the treatment of cancer.

SUMMARY OF THE INVENTION

Surprisingly, positive and preferably even highly synergistic effects between PKC-, especially PKC-α-targeted oligonucleotides or oligonucleotide derivatives (ODNs) and standard chemotherapeutic drugs have been observed in nude mouse xenograft models. It is thus reasonable to assume that the ODNs might be used not only as single agents, but also especially in combination therapy for the treatment of cancer diseases.

This combination offers a lot of advantages: In the first place, standard chemotherapeutics often display significant side effects up to really toxic effects, so that their use alone is often very difficult in order to obtain a responsible balance between therapeutic use and side effects. In the new combinations decribed herein, however, it is possible to diminish the amount of standard chemotherapeutic needed and thus to alleviate side effects. Second, the ODNs have a very high tolerability (up to 100 mg/kg have been found to be non-toxic in animals), thus allowing great flexibility in the treatment of cancer patients. Third, due to the fact that the PKC-, especially PKC-α-directed ODNs open up a totally new route of treatment, it is also possible to treat cancer types which have been very difficult to treat or even practically unaffected by therapy with standard chemotherapeutics, such as small cell lung carcinomas, large cell lung carcinomas, melanomas, prostate carcinomas and also breast cancer. Fourth, in a number of cases it is even possible to bring about regression of tumors and complete cure. Most importantly, practically no antagonistic effects are observed in the combination experiments.

DETAILED DESCRIPTION OF THE INVENTION

The present invention preferably relates to combination preparations comprising a) at least one oligonucleotide or oligonucleotide derivative (ODN) targeted to nucleic acids encoding (especially human) PKC with b) at least one other chemotherapeutic agent; or pharmaceutically acceptable salts of any component a), b) or a) and b) if at least one salt-forming group is present.

The invention also relates to a method for treating a proliferative disease that can be treated by administration of an oligonucleotide or oligonucleotide derivative targeted to PKC, especially PKC-α, especially where the disease responds to modulation of PKC, especially PKC-α, activity, where a) at least one oligonucleotide or oligonucleotide derivative (ODN) targeted to nucleic acids encoding (especially human) PKC and capable of modulating (especially human) PKC expression and b) at least one other chemotherapeutic agent are administered to a mammal in combination in a quantity which is jointly therapeutically effective against proliferative diseases that can be treated by administration of an oligonucleotide or oligonucleotide derivative targeted to PKC, especially PKC-α, or that preferably depend on PKC, especially PKC-α, activity in order to treat them, where any component a) and/or b) can also be present in the form of a pharmaceutically acceptable salt, if at least one salt-forming group is present.

The invention also relates to a product which comprises
a) at least one oligonucleotide or oligonucleotide derivative (ODN) targeted to nucleic acids encoding (especially human) PKC, especially PKC-α, and
b) at least one other chemotherapeutic agent where any component a) and/or b).can also be present in the form of a pharmaceutically acceptable salt, if at least one salt-forming group is present, in the presence or absence of one or more pharmaceutically acceptable carrier materials, as a combination preparation for simultaneous or chronologically staggered use within a period of time which is small enough for the active compounds both of component a) and of component b) to mutually enhance antiproliferative activity against proliferating cells, especially in a patient, for treating a proliferative disease which responds to such active compounds.

The invention also relates to a pharmaceutical preparation which comprises a quantity, which is jointly effective for treating a proliferative disease that can be treated by administration of an oligonucleotide or oligonucleotide derivative targeted to PKC, especially PKC-α (preferably that can be treated by modulation of (especially human) PKC, especially PKC-α, activity), of
a) at least one oligonucleotide or oligonucleotide derivative (ODN) targeted to nucleic acids encoding PKC, especially PKC-α, and
b) at least one other chemotherapeutic agent, where any component a) and/or b) can also be present in the form of a pharmaceutically acceptable salt, if at least one salt-forming group is present, with one or more pharmaceutically acceptable carrier materials.

The invention also relates to the use of a combination of
a) at least one oligonucleotide or oligonucleotide derivative (ODN) targeted to nucleic acids encoding PKC, especially PKC-α, and
b) at least one other chemotherapeutic agent, where any component a) and/or b) can also be present in the form of a pharmaceutically acceptable salt, if at least one salt-forming group is present, for producing pharmaceutical preparations for use as compositions against a proliferative disease that can be treated by administration of an oligonucleotide or oligonucleotide derivative targeted to PKC, especially PKC-α, preferably a proliferative disease that can be treated by modulation of PKC (especially PKC-α) activity.

Included is use in a method of inhibiting hyperproliferation of cells comprising contacting hyperproliferating cells with a pharmaceutical preparation or product as specified in the last two paragraphs, especially a method of treating a proliferative disease comprising contacting a subject, cells, tissues or a body fluid of said subject, suspected of having a hyperproliferative diesease with a pharmaceutical composition or product as specified in the last two paragraphs.

The term "at least one" taking reference to a) oligonucleotides or oligonucleotide derivatives or b) other chemotherapeutic agents refers to one or more, especially 1 to 5, members of each group a) or b), preferably to one compound of group a) and 1 or more, especially 1 to 5, most especially 1 or 2 compounds of group b).

An oligonucleotide or oligonucleotide derivative (ODN) targeted to nucleic acids encoding (especially human) PKC is primarily characterized as follows: The relationship between an such an ODN and its complementary nucleic acid target to which it hybridizes is commonly referred to as "antisense". "Targeting" an oligonucleotide to a chosen nuclei acid target, in the context of this invention, is a multistep process. The process usually begins with identifying a nucleic acid sequence of which the function is to be modulated. This may be, as examples, a cellular gene or especially a mRNA made from that gene the expression of which is associated with a particular disease state, or for a foreign nucleic acid from an infectious agent. In the present invenion, the target is a nucleic acid encoding PKC, that is, the PKC gene or preferably the mRNA expressed from the PKC gene. The targeting process also includes determination of the site or sites within the nucleic acid sequence for the oligonucleotide interaction to occur in such a way that the desired effect-modulation of gene-expression will result. Once the target site or target sites have been identified, oligonucleotides are selected which are sufficiently complementary to the target, i.e., that hybridize sufficiently well and show sufficiently specific hybridization to provide the desired modulation. By the term "PKC" there is meant any isoenzyme of PKC, preferably human PKC, especially human PKC-α.

In the context of this invention, the term "modulation" means either stimulation or preferably inhibition. Inhibition of PKC gene expression is the preferred form of modulation. This modulation can be measured in ways which are routine in the art, for example by Northern blot assay of mRNA expression or Western blot assay (see, for example, Sambrook, Fritsch and Maniatis, "Molecular Cloning: A Laboratory Manual" 2nd edition, Cold Spring Harbor Laboratory Press, 1989; see also International Application WO 95/32987). Effects on tumor growth can be measured in analogy to or in accordance with the processes taught in the examples of the present application. "Hybridization", in the context of this invention, means hydrogen bonding, also known as Watson-Crick base-pairing, between complementary bases, usually on opposite nucleic acid strands or two regions of a nucleic acid strand. Guanine and cytosine are examples of complementary bases which are known to form three hydrogen bonds between them. Adenine and thymine or adenine and uracil are examples of complementary bases which form two hydrogen bonds between them. "Specifically hybridizable" and "complementary" are terms used to indicate a sufficient degree of complementarity such that stable and specific binding occurs between the DNA and RNA target and the ODN. It is understood that an ODN need not be 100% complementary o its target nucleic acid sequence to be specifically hybridizable. An oligonucleotide is specifically hybridizable when binding of the oligonucleotide to the target interferes with the previously uninfluenced function of the target molecule to cause a loss of its effectiveness, and there is a sufficient degree of complementarity to avoid non-specific binding of the oligonucleotide to non-target sequences under conditions in which specific binding is desired, i.e. under physiological conditions in the case of in vivo application or therapeutic treatment (or, in the case of in vitro assays, under conditions in which the assays are conducted).

In vitro hybridization conditions are known in the art and can be found, inter alia, in the reference given below for Northern blotting or in Maniatis et al., "Molecular Cloning—A Laboratory Manual", second edition, Cold Spring Harbor Laboratory Press, 1989, vol. 2, 9.47 to 9.58. For example, the respective cDNA can be immobilized on nitrocellulose filters. Prehybridization (to reduce nonspecific background binding) is possible as a first step, for example using a mixture comprising 6×SSC (prepared by dilution of 20×SSC=175.3 g of NaCl and 88.2 g of sodium citrate in 800 ml of H$_2$O, pH adjusted by a few drops of 10M NaOH to 7.0, volume adjusted with H$_2$O to 1l)/5X Denhardt's reagent (prepared by tenfold dilution with 6×SSC of a solution of 5 g of Ficoll (Type 400, Pharmacia, Sweden), 5 g of polyvinylpyrrolidone, 5 g of bovine serum albumin (Pentex Fraction V) and H$_2$O to 500 ml)/0.5 sodium dodecylsulfate (=SDS)/10 mg denatured, fragmented salmon sperm DNA (Sigma type III sodium salt (10 mg/ml) is dissolved in water, if necessary, stirring with a magnetic stirrer at room temperature; the solution is adjusted to 0.1M NaCl and extracted once with phenol and once with phenol/chloroform; the aqueous phase is recovered and the DNA is sheared by passing it 12 times rapidly through a 17-gauge hypodermic needle; the DNA is precipitated by adding two volumes of ice-cold ethanol; it is then recovered by centrifugation and redissolved at a concentration of 10 mg/ml in water; the OD$^{260}$ is determined and the exact concentration of the DNA is calculated; the solution is then boiled for 10 minutes and stored at −20° C. in small aliquots; just before use, the solution is heated for 5 min in a boiling-water bath and then chilled quickly in ice water; denatured, fragmented salmon sperm DNA is preferably used at a concentration of 100 mg/ml hybridization solution) and, if desired, 50% formamide. The prehybridization solution is preferably filtered through a 0.45 micrometer disposable cellulose acetate filter (e.g. Schleicher and Schuell Uniflow syringe filter No. 57240 or equivalent).

The nitrocellulose filter is then floated on the surface of a tray of 6×SSC until it is thoroughly wetted and is then submerged for 2 min. The wet filter is slipped in a heat-sealable bag (e.g. Sears Seal-A-Meal or equivalent). 2 ml of prehybridization solution/cm$^2$ filter are added. Air is squeezed from the filter, and the open end of the bag is heat-sealed. The bag is incubated for 1–2 h at 68° C. (for aqueous solvents) or 42° C. (in the presence of 50% formamide). The bag containing the filter is removed from the water bath and opened by cutting off one corner with scissors. The labeled probe (e.g. a $^{32}$P-labeled nucleotide or preferably nucleotide derivative according to the invention) is added to the prehybridization solution and air is removed by squeezing. The bag is resealed (entrapping as few bubbles as possible). The bag is submerged in water bath at the required temperature for the required time of hybridization. Then the bag is opened at a corner. After removal of the hybridization solution, the filter is removed and submerged in several hundred ml of 2×SSC and 0.5% SDS at room temperature for some minutes not allowing the filter to dry; this treatment is repeated with fresh solution. Then the filter is incubated in 0.1×SSC/0.5% SDS for 30 to 60 min at 37° C. with gentle agitation. The solution is replaced by a fresh aliquot and incubation at 68° C. follows for 30 to 60 min. The amount of radioactivity can then be determined on X-ray films (e.g. Kodak XAR-2 or equivalents) to obtain an autoradiographic image.

Preferably, an ODN is employed which is targeted to human mRNA encoding PKC-α (preferably corresponding to the sequence given in Finzenkeller et al., Nucleic Acids Res. 18: 2183–2183, 1990). Persons of ordinary skill in the art will be aware that mRNA includes not only the coding region which carries the information to encode a protein using the three letter genetic code, but also associated ribonucleotides which form a region known as the 5'-untranslated region, the 3'-untranslated region, the 5'-cap region, intron regions and intron/exon or splice junction ribonucleotides. Thus, oligonucleotides may preferably be formulated which are targeted wholly or in part to these associated ribonucleotides. In preferred embodiments, the oligonucleotide is targeted to a translation initiation site (AUG codon) or sequences in the 5'- or 3'-untranslated region of the human PKC-α mRNA. The functions of messenger RNA to be interfered with include all vital functions such as translocation of the RNA to the site for protein translation, actual translation of protein from the RNA, splicing or maturation of the RNA and possibly even independent catalytic activity which may be engaged in by the RNA. The overall effect of such interference with the RNA function is to cause interference with PKC protein expression. More preferred among the ODNs are those that correspond to the 3'-untranslated region of the human PKC-α mRNA.

The term "correspond" means that the given compound has base pairing characteristics comparable to the nucleic acid sequence referred to, that is, comparable hybridization characteristics.

Antisense oligonucleotides or oligonucleotide derivatives for combination according to the invention comprising nucleotide units or analogues/derivatives thereof sufficient in number and identity to allow hybridization preferably have a length that allows specific binding to the target sequence, especially a length corresponding to 5 to 50 nucleotide units, preferably to 10 to 35 nucleotide units, more preferably to 15 to 22 nucleotide units, and most preferably to 18 to 21 nucleotide units.

In order to allow also for the inclusion of allelic variants of the human PKC, especially PKC-α, gene and for hybridizable oligonucleotides or oligonucleotide analogues that show minor numbers of mispairing that still allow hybridization, the sequences can vary from those corresponding to the human PKC-α mRNA (preferably corresponding to the sequence given in Finzenkeller et al., Nucleic Acids Res. 18, 2183–2183 (1990)) by some nucleotides or nucleotide analogues; preferably, up to 3 nucleotides or nucleotide analogues can differ in the sequence of a given oligonucleotide or oligonucleotide derivative with respect to the corresponding PKC cDNA, more preferably in the sense of conservative mutations.

Preferred is an oligonucleotide or oligonucleotide derivative as published in any one of International Applications WO 93/19203 or WO 95/02069, especially in the examples thereof, or a salt thereof.

Most preferred is an oligonucleotide or oligonucleotide derivative that corresponds to the following sequence, or a salt thereof:

5'-GTT CTC GCT GGT GAG TTT CA -3'      SEQ.-ID NO: 1.

It is evident that also shortened and/or shifted versions of this sequence are encompassed, especially those which show hybridization as defined above, e.g. derivatives with 15 to 20 of the abovementioned building blocks. "Shortened" means preferably that the sequence is shortened terminally on one or both ends.

Generally, oligonucleotide derivatives, especially oligo-2-'deoxynucleotide derivatives, are preferred over oligonucleotides as such.

The oligonucleotides or oligonucleotide derivatives used in a combination according to the invention can be designed to selectively inhibit a given isozyme or particular set of isozymes of human PKC, or to inhibit all members of a given family of isozymes of human PKC, especially PKC-α.

The oligonucleotides or their derivatives can be isomerically pure or they can be present in isomeric mixtures. Thus, if asymmetric phosphorus atoms are present, the compounds can be present as diastereomeric mixtures or as pure diastereomers.

Some of the oligonucleotides or oligonucleotide derivatives can be present in different tautomeric forms, depending inter alia on the solvent and the ionization status of ionizable groups. Thus, for example, the central group in phosphorothioates [O—(P—SH)(=O)—O] being tautomerizable to [O—(P=S)(—OH)—O] with the more stable form depending, among others, on the solvent and the state of ionization. Within the present specification, the term oligonucleotide derivatives is also to be understood to encompass these tautomeric forms, the presence of which is know to the person skilled in the art.

The prefix "lower" denotes a radical with up to and including 7 carbon atoms, preferably up to and including 4, and most preferably with up to and including 2 carbon atoms, if not indicated otherwise.

A nucleotide unit is a base-sugar or base-sugar analogue combination suitably bound to an adjacent nucleotide unit through phosphodiester or other bonds.

In the context of this invention, the term "oligonucleotide" refers to an oligonucleotide formed from naturally occurring base radicals and pentofuranosyl (ribosyl or (preferably) 2'-deoxyribosyl) groups or modified forms thereof joined by native phosphodiester bonds, that is which comprises building blocks of the following formulae I and/or I* wherein Q is H or OH:

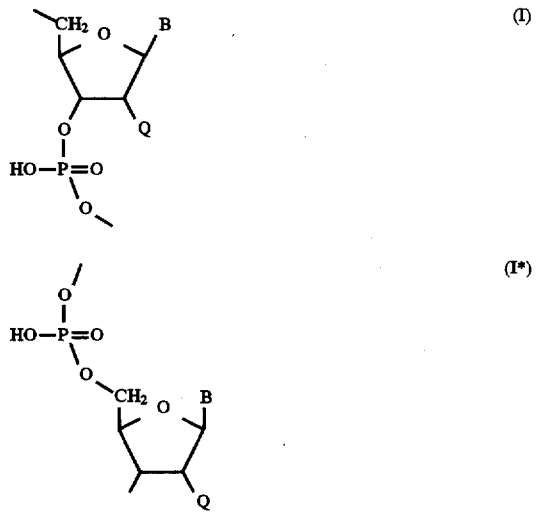

wherein B is a radical of a base selected from thymine, uracil, 5-propynyluracil, cytosine, 5-methylcytsine, 5-propynylcytosine, adenine, 2-aminoadenine and guanine.

The term "oligonucleotide derivative" refers to synthetic species derived from naturally occurring nucleotide subunits or their close homologues and may also refer to moieties which function similarly to naturally occurring oligonucleotides but which have non-naturally occurring portions, for example at least one building block that differs from the building blocks of a natural oligonucleotide. Thus, oligonucleotides with regard to their backbone may have altered sugar moieties and/or inter-sugar linkages, and, with regard to the bases, altered bases may be present.

Such oligonucleotide derivatives are best described as being functionally interchangeable with natural oligonucleotides (or synthesized oligonucleotides along natural lines), but having one or more differences from natural structure. All such oligonucleotides are comprehended within this invention so long as they function effectively to show the hybridization properties to DNA or RNA deriving from the PKC-, especially the PKC-α gene, preferably to mRNA.

With regard to the backbone, that is to the altered sugar moieties and/or inter-sugar linkages (internucleosidic bridges), preferred among these are the following types:

Species derived from naturally occurring nucleotide subunits or their close homologues of formula I or I* wherein B is a base radical as defined below and Q is H, OH, SH, SCH3, F, $N_3$, CN, OCN, $OCH_3$, $O(CH_2)_zNH_2$ or $O(CH_2)_zCH_3$ where z is from 1 to about 10, $O(CH_2CH_2O)_vCH_3$ wherein v is from 0 to 12, especially 1 or 3, $CH_2CH(CH_3)OCH_3$ or $CH_2CH(OH)CH_2OH$, or in a broader sense another substituent having similar properties, for example selected from Cl, Br, $CF_3$, $ONO_2$, $NO_2$, $NH_2$ and O—, S— or NH-lower alkyl, most especially Q being hydroxy, F, methoxy, (preferably) 2'-(2-methoxy)ethoxy, or (more preferably) hydrogen;

phosphorothioate and in a broader sense other species such as phosphorodithioate, sulfate, sulfonate, sulfonamide, sulfone, sulfite, sulfoxide, sulfide, formacetal, 3'-thioformacetal, 5'-thioether, hydroxylamine (with $CH_2$—NH—O—$CH_2$ instead of the phosphodiester bond O—[(HO—)P(=O)]—O—$CH_2$), methylene(methylimino) (with $CH_2$—$N(CH_3)$—O—$CH_3$ instead of the phosphodiester bond); methyleneoxy(methylimino) (with $CH_2$—O—$N(CH_3)$—$CH_2$ instead of the phosphodiester bond), methylene-((methylimino)-methylimino) (with $CH_2$—$N(CH_3)$—$N(CH_3)$—$CH_2$ instead of the phosphodiester bond), carbonate, 5'-N-carbamate, amide (with $CH_2$—(C=O)—NH—$CH_2$ instead of the phosphodiester bond, see International Application WO 92/20823), morpholinocarbamate (see Summerton, J. E. and Weller, D. D., U.S. Pat. No: 5,034,506) or peptide nucleic acid (see P. E. Nielsen, M. Egholm, R. H. Berg, O. Buchardt, Science 254, 1497 (1991)) which are known for use in the art (for reviews with references concerning these modified nucleotides, see Milligan et al., J. Med. Chem. 36(14), 1923–37 (1993), and Uhlmann et al., Chemical Reviews 90(4), 543–84 (1990)). In accordance with some preferred embodiments, at least one of the phosphodiester bonds of the oligonucleotide has been substituted with a structure which functions to enhance the ability of the compositions to penetrate into the region of cells where the RNA or DNA whose activity to be modulated is located and in order to avoid extensive degradation of the oligonucleotide derivative due to nucleases that would result in ineffective cleavage products. It is preferred that such substitutions comprise phosphorothioate bonds, phosphorodithioate bonds, methyl phosphonate bonds, phosphoramidate bonds, amide bonds, boranophosphate bonds, phosphotriester bonds, short chain alkyl or cycloalkyl structures, or heteroatom-substituted short chain alkyl structures, and most especially phosphorothioate bonds or amide bonds.

Preferred of these are oligonucleotide derivatives which (in their nucleotide/nucleotide derivative sequence) comprise at least one of the following units (bivalent radicals) of the formulae given hereinafter, wherein B is a base radical as defined below; Q is H, OH, SH, SCH3, F, $N_3$, CN, OCN, $OCH_3$, $O(CH_2)_zNH_2$ or $O(CH_2)_zCH_3$ where z is from 1 to about 10, $O(CH_2CH_2O)_vCH_3$ wherein v is from 0 to 12, especially 1 or 3, $CH_2CH(CH_3)OCH_3$ or $CH_2CH(OH)CH_2OH$, or in a broader sense another substituent having similar properties, for example selected from Cl, Br, $CF_3$, $ONO_2$, $NO_2$, $NH_2$ and O—, S— or NH-lower alkyl, most especially Q being hydroxy, methoxy, F or (preferably) —O—$CH_2CH_2OCH_3$ or (most preferably) hydrogen; and the other moieties have the meanings given behind the respective formula:

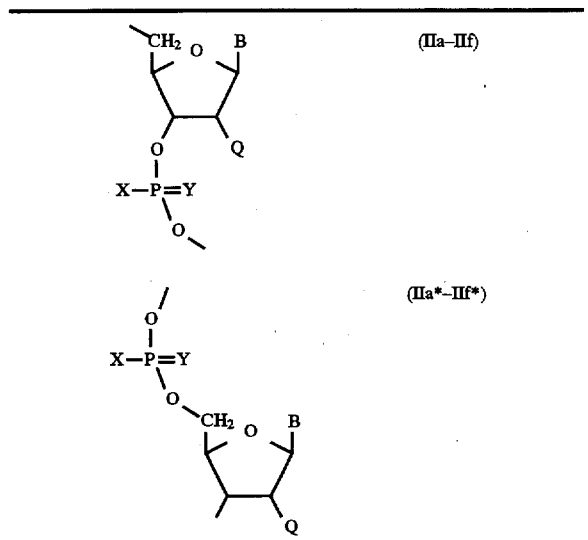

| Radical of formula | type | | |
|---|---|---|---|
| (IIa), (IIa*) | phosphorothioate | X=SH | Y=O |
| (IIb), (IIb*), | phosphorodithioate | X=SH | Y=S |
| (IIc), (IIc*), | methylphosphonate | X=$CH_3$ | Y=O |
| (IId), (IId*), | phosphoramidate | X=NH—R | Y=O |
| (IIe), (IIe*), | boranophosphate | X=$BH_3$ | Y=O |
| (IIf), (IIf*) | phosphotriester | X=O—R | Y=O | wherein R is lower alkyl;

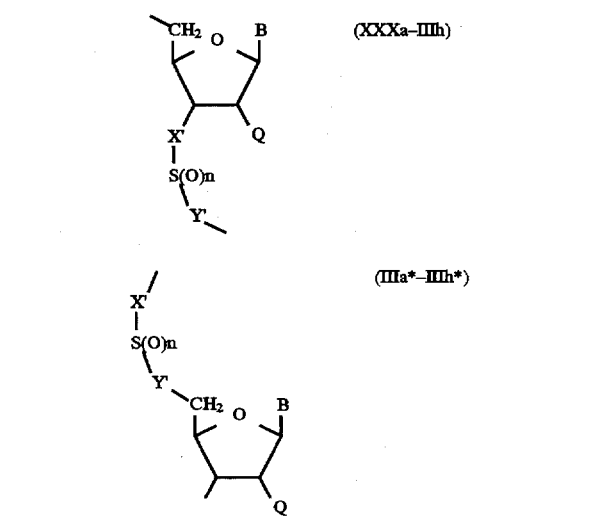

| Radical of formula | type | n | X' | Y' |
|---|---|---|---|---|
| (IIIa), (IIIa*) | sulfate | 2 | O | S |
| (IIIb), (IIIb*), | sulfonate | 2 | O | $CH_2$ |
| (IIIc), (IIIc*), | sulfamate | 2 | O | NH |
| (IIId), (IIId*), | sulfonamide | 2 | NH | $CH_2$ |
| (IIIe), (IIIe*), | sulfone | 2 | $CH_2$ | $CH_2$ |
| (IIIf), (IIIf*) | sulfite | 1 | O | O |
| (IIIg), (IIIg*) | sulfoxide | 1 | $CH_2$ | $CH_2$ |
| (IIIh), (IIIh*) | sulfide | 0 | $CH_2$ | $CH_2$ |

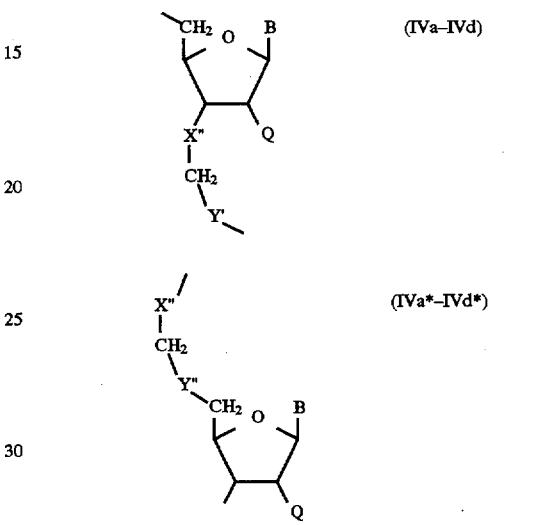

| Radical of formula | type | X" | Y" |
|---|---|---|---|
| (IVa), (IVa*) | formacetal | O | O |
| (IVb), (IVb*) | 3'-thioformacetal | S | O |
| (IVc), (IVc*) | 5'-thioformacetal | O | S |
| (IVd), (IVd*) | thioether | $CH_2$ | S |

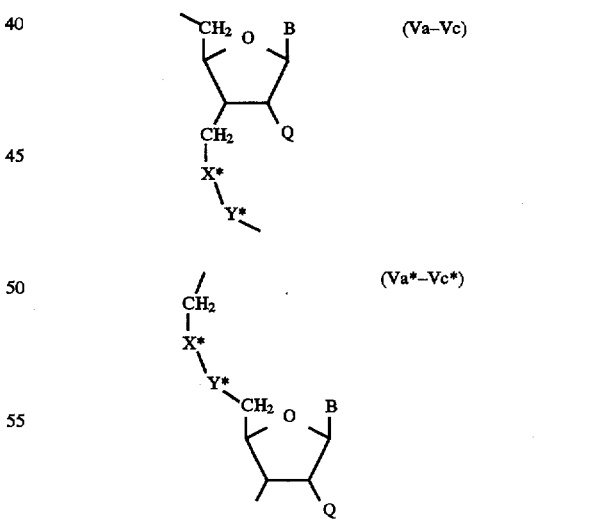

| Radical of formula | type | X* | Y* |
|---|---|---|---|
| (Va), Va*) | hydroxylamine | N—H | O |
| (Vb), Vb*) | methylene(methyl-imino) | N—$CH_3$ | O |
| (Vc), Vc*) | methyleneoxy(methyl-imino) | O | N—$CH_3$ |

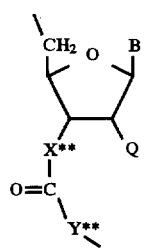 (VIa–VId)

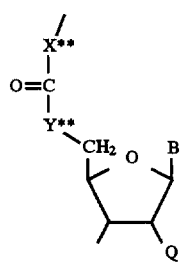 (VIa*–VId*)

| Radical of formula | type | X | Y |
|---|---|---|---|
| (VIa), VIa*) | carbonate | O | O |
| (VIb), VIb*) | 5'-N-carbamate | O | NH |
| (VIc), VIc*) | amide | CH$_2$ | N(A) |
| (VId), VId*) | amide II | NH | CH$_2$ | wherein A is H, methyl or phenyl, preferably H;

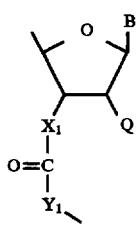 (VII)

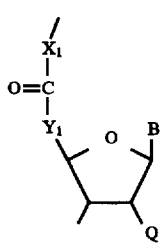 (VII*)

| Radical of formula | type | X$_1$ | Y$_1$ |
|---|---|---|---|
| (VII), (VII*) | amide III | NH | CH$_2$ |

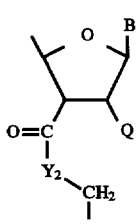 (VIII)

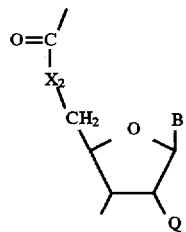 (VIII*)

| Radical of formula | type | X$_2$ |
|---|---|---|
| (VIII), (VIII*) | amide IV | NH |

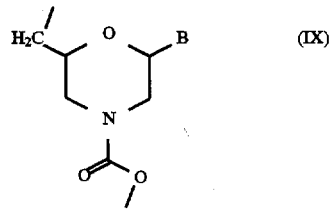 (IX)

(IX*)

| Radical of formula | type |
|---|---|
| IX, IX* | morpholino-carbamate |

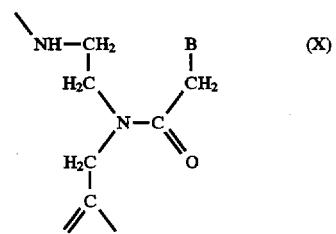 (X)

(X*)

| Radical of formula | type |
|---|---|
| X, X* | peptide nucleic acid |

The oligonucleotide derivatives can be composed of a combination of these units, or they can preferably (i) be chimeric oligonucleotides or (ii) comprise only one type of these units with regard to the backbone (sugar moieties and/or inter-sugar linkages) which is present throughout the chain of the respective oligonucleotide derivative, preferably oligo-2'deoxynucleotide derivative, most preferably of the 2'-deoxyribose-phosphorothioate type. At the 5'-and 3'-termini of the respective oligonucleotide derivative molecules, the free valency of the radicals of any of the above formulae I, I*, II to X and II* to X* is bonded preferably to hydrogen if the terminal atom is selected from N, O and S and to hydroxy or an analogue thereof, such as halogen, for example Cl, Br or I, mercapto (SH) or azido ($N_3$), if the terminal atom is C, more preferably to one of the following residues, but may also (in a broader aspect of the invention) be bound to other conjugated moieties as described below forming conjugates. Both groups (i) and (ii) are also preferred independently as separate group.

The "chimeric oligonucleotides" or "chimerae", in the context of this invention, are oligonucleotides which contain two or more chemically distinct regions, each made up of at least one oligonucleotide or oligonucleotide derivative. These oligonucleotides typically contain at least one region of modified nucleotides that confers one or more beneficial properties (such as, for example, increased nuclease resistance, increased uptake into cells, increased binding affinity for the RNA target, diminished probability for sequence independent side effects), the so-called wing, and a region that permits RNase H mediated cleavage of the target complement, the so-called RNase H-window. In one embodiment, a chimeric oligonucleotide comprises at least one region modified to increase target binding affinity and, usually, a region that permits RNase H mediated cleavage of the target complement. Affinity of an oligonucleotide or an oligonucleotide derivative for its target is routinely determined by measuring the Tm of an oligonucleotide/target pair, which is the temperature at which the oligonucleotide or its derivative and the target dissociate. Dissociation is detected spectrophotometrically. The higher the Tm, the greater the affinity of the oligonucleotide for the target. Methods for Tm measurement are known in the art (see, e.g., Sambrook, Fritsch and Maniatis, "Molecular Cloning—A Laboratory Manual", 2nd edition, Cold Spring Harbor Laboratory Press, 1989). Such modified regions M are routinely incorporated into oligonucleotides and these oligonucleotides have been shown to have a higher Tm (i.e., a higher target binding affinity) than 2'-deoxyoligonucleotides against a given target. The effect of such increased affinity is to greatly enhance antisense oligonucleotide inhibition of raf gene expression. RNase H is a cellular endonuclease that cleaves the RNA strand of RNA:DNA duplexes. Activation of this enzyme therefore results in cleavage of the RNA target, and can thus greatly enhance the efficiency of antisense inhibition. Cleavage of the RNA target can be routinely demonstrated by gel electrophoresis. In another embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides or derivatives thereof with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. In some cases, oligonucleotide modifications which enhance target binding affinity are also, independently, able to enhance nuclease resistance. Especially preferred is the 2'—O—$CH_2CH_2OCH_3$ (2'-(2-methoxy)ethoxy) modification at the 2' position of at least one oligonucleotide. This modification has been shown to increase both the affinity for its target and nuclease resistance of the oligonucleotide.

Chimeric oligonucleotides preferably show, on the one hand, M regions of between 3 and 20 (preferably 5 to 15) modified building blocks (either with phosphodiester or with phosphorothioate backbone), especially with 2'-modification, especially 2'-(2-methoxy)ethoxy or 2'-F modified building blocks, which are in succeeding order; and, on the other hand, U regions of 4 to 20 2'-deoxy building blocks with phosphorothioate structure that are otherwise unmodified. Preferably, the M and U regions can be in one of the following arrangements:

5'-M-U-M-3'

5'-M-U-3' or

5'-U-M-3'.

In compounds with a terminal moiety of any one of the formulae I, IIa-IIh, IIIa, IIIc, IIIf, IVa-IVd, Va-Vc, VIa-VIc, IX and X*, the 5' terminus is preferably bonded to a terminal OH group, and the 3'-terminus to a hydrogen.

In compounds with a terminal moiety of any one of the formulae I*, IIa*-IIh*, IIIa*-IIIh*, IVa*-IVc*, Va*-Vc*, VIa*-VId, VII*, VIII* and X, the 5'-terminus is preferably bonded to a terminal hydrogen, and the 3'-terminus to a OH group.

In compounds with a terminal moiety of the formula VIe, both the 5' and the 3' terminus are preferably bonded to a terminal hydrogen.

In compounds with a terminal moiety of any one of the formulae IX*, the 5'-terminus is preferably bonded to a terminal OH group which is bonded replacing the terminal —(C=O)—O, and the 3'-terminus to a hydrogen atom.

In compounds with a terminal moiety of any one of the formulae IIIb, IIId, IIIe, IIIe*, IIIg, IIIg*, IIIh, IIIh*, IVd*, VId, VII, VIII and VIII*, the 5'-terminus is preferably bonded to a terminal OH group and the 3'-terminus is preferably bonded to an OH group.

In order to allow for modified and improved pharmacokinetic properties, such as enhanced uptake into cells or the oligonucleotides or oligonucleotide derivatives in combinations according to the invention can also be conjugated to one or more (then identical or different) additional moieties, for example selected from: A group forming micelles, an antibody, a carbohydrate, a receptor-binding group, a steroid, such as cholesterol, a polypeptide, an intercalating agent, such as an acridine derivative, a long-chain alcohol, a phospholipid and other lipophilic groups.

The very most preferred of the oligonucleotide (preferably oligo-2'-deoxyoligonucleotide) derivatives are those of the phosphorothioate type.

B in any of the formulae (Ii) to (Xi) and (Ii*) to (Xi*) ("i" standing for the respective indices in the formulae above or below, such as, for example, "a", "b" or no index if none is required) is a base radical and is selected from the group comprising a purine radical or an analogue thereof and a pyrimidine radical or an analogue thereof.

If B is a purine radical or an analogue thereof, it may be a radical of formula XI, XIa, XIb, XIc, XId, XIe or XIf

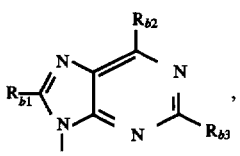 (XI)

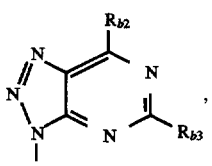 (XIa)

 (XIb)

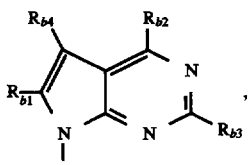 (XIc)

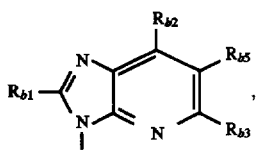 (XId)

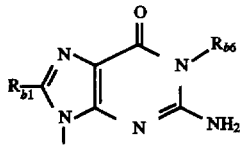 (XIe)

or

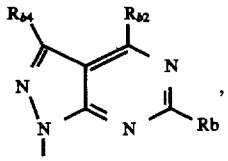 (XIf)

wherein $R_{b1}$ is H, Cl, Br, OH or —O—$C_1$–$C_{12}$alkyl, and $R_{b2}$, $R_{b3}$ and $R_{b5}$ are each independently of the others H, OH, SH, $NH_2$, $NHNH_2$, NHOH, NHO—$C_1$–$C_{12}$alkyl, —N=CH—N($C_1$–$C_{12}$alkyl)$_2$, F, Cl, Br, $C_1$–$C_{12}$alkyl, hydroxy-$C_1$–$C_{12}$alkyl, amino-$C_1$–$C_{12}$alkyl, $C_1$–$C_{12}$alkoxy, benzyloxy or $C_1$–$C_{12}$alkylthio, the hydroxy and amino groups being present as such or substituted by a protecting group; or phenyl, benzyl, primary amino having from 1 to 20 carbon atoms or secondary amino having from 2 to 30 carbon atoms, $R_{b4}$ is hydrogen, CN or —C≡C—$R_{b7}$, and $R_{b6}$ and $R_{b7}$ are hydrogen or $C_1$–$C_4$alkyl.

Protecting groups and processes for derivatising amino groups (as well as imino groups, "amino" groups in the following paragraphs that refer to amino protecting groups also, if possible, meaning imino) having such protecting groups are generally known in sugar, amino acid and nucleotide chemistry and are described, for example, in standard text books (see J. F. W. McOmie, "Protective Groups in Organic Chemistry", Plenum Press, London and New York 1973; Th. W. Greene, "Protective Groups in Organic Synthesis", Wiley, N.Y. 1981, in "The Peptides", Volume 3 (E. Gross and J. Meienhofer, eds.), Academic Press, London and New York 1981; Greene, B. T., "Protective Groups in Organic Synthesis", Wiley Interscience, New York (1991), Sonveaux, E., Bioorganic Chemistry 14, 274–325 (1986), Beaucage, S. L., et al., Tetrahedron 48, 222, "Methoden der organischen Chemie", Houben-Weyl, 4th edition, Volume 15/I, Georg Thieme Verlag, Stuttgart 1974; and H. -D. Jakubke and H. Jescheit, "Aminosäuren, Peptide, Proteine" ("Amino acids, peptides, proteins"), Verlag Chemie, Weinheim, Deerfield Beach and Basle 1982). Examples of such protecting groups are: benzyl, methylbenzyl, dimethylbenzyl, methoxybenzyl, dimethoxybenzyl, bromobenzyl, 2,4-dichlorobenzyl; diphenylmethyl, di(methylphenyl)methyl, di(dimethylphenyl)methyl, di(methoxyphenyl)methyl, di(dimethoxyphenyl)methyl, triphenylmethyl, tris-4,4',4"-tert-butyl-phenylmethyl, di-p-anisylphenylmethyl, tri(methylphenyl)methyl, tri(dimethylphenyl)methyl, methoxyphenyl(diphenyl)methyl, di(methoxyphenyl)phenylmethyl, tri(methoxyphenyl)methyl, tri(dimethoxyphenyl)methyl; triphenylsilyl, alkyldiphenylsilyl, dialkylphenylsilyl and trialkylsilyl having from 1 to 20, preferably from 1 to 12, and especially from 1 to 8, carbon atoms in the alkyl groups, for example trimethylsilyl, triethylsilyl, tri-n-propylsilyl, isopropyl-dimethylsilyl, tertbutyl-dimethylsilyl, tert-butyl-diphenylsilyl, n-octyl-dimethylsilyl, (1,1,2,2-tetramethylethyl)dimethylsilyl; —($C_1$–$C_8$alkyl)$_2$Si—O—Si($C_1$–$C_8$alkyl)$_2$—, wherein alkyl is, for example, methyl, ethyl, n- and iso-propyl or n-, iso- or tert-butyl; $C_2$–$C_{12}$acyl, especially $C_2$–$C_8$acyl, such as acetyl, propanoyl, butanoyl, pentanoyl, hexanoyl, benzoyl, methylbenzoyl, methoxybenzoyl, chlorobenzoyl and bromobenzoyl; $R_{S1}$—$SO_2$— wherein $R_{S1}$ is $C_1$–$C_{12}$alkyl, especially $C_1$–$C_6$alkyl, $C_5$- or $C_6$-cycloalkyl, phenyl, benzyl, $C_1$–$C_{12}$alkyl-phenyl, especially $C_1$–$C_4$alkyl-phenyl, or $C_1$–$C_{12}$alkyl-benzyl, especially $C_1$–$C_4$alkyl-benzyl, or halophenyl or halobenzyl, for example methyl-, ethyl-, propyl-, butyl-, phenyl-, benzyl-, p-bromo-, p-methoxy- and p-methylphenyl-sulfonyl; $C_1$–$C_{12}$alkoxycarbonyl, preferably $C_1$–$C_8$alkoxycarbonyl, that is unsubstituted or substituted by F, Cl, Br, $C_1$–$C_4$alkoxy, tri($C_1$–$C_4$alkyl)silyl or by $C_1$–$C_4$alkylsulfonyl, for example methoxy-, ethoxy-, n- or iso-propoxy- or n-, iso- or tert-butoxycarbonyl, 2-trimethylsilylethoxycarbonyl, 2-methylsulfonylethoxycarbonyl, allyloxycarbonyl, or phenoxycarbonyl or benzyloxycarbonyl that is unsubstituted or is substituted as for alkoxycarbonyl, for example methyl- or methoxy- or chloro-phenoxycarbonyl or methyl- or methoxy- or chloro-benzyloxycarbonyl, and 9-fluorenylmethoxycarbonyl. If a hydroxy protecting group is alkyl, this moiety may be substituted by fluorine, chlorine, bromine, $C_1$–$C_4$alkoxy, phenoxy, chlorophenoxy, methoxyphenoxy, benzyloxy, methoxybenzyloxy or by chlorophenoxy. If more than one hydroxy group is protected in the respective oligonucleotide or its derivative, the protecting groups may be identical or different.

A protected amino group may be protected, for example, in the form of an acylamino, aryl-methylamino, etherified mercaptoamino, 2-acyl-lower alk-1-enylamino, silylamino or N-lower alkylpyrrolidinylidene group or in the form of an azido group.

In a corresponding acylamino group, acyl is, for example, the acyl radical of an organic carboxylic acid having, for example, up to 18 carbon atoms, especially an unsubstituted or substituted, for example halo- or aryl-substituted, lower alkanecarboxylic acid or an unsubstituted or substituted, for example halo-, lower alkoxy- or nitro-substituted, benzoic acid, or, preferably, of a carbonic acid semiester. Such acyl groups are, for example, lower alkanoyl, such as formyl, acetyl, propionyl, isobutyryl or pivaloyl, halo-lower alkanoyl, for example 2-haloacetyl, such as 2-chloro-, 2-bromo-, 2-iodo-, 2,2,2-trifluoro- or 2,2,2-trichloro-acetyl, phenyoxy- or (lower alkoxy)phenoxy-lower alkyl, such as phenoxyacetyl or 4-tert-butylphenoxyacetyl, unsubstituted or substituted, for example halo-, lower alkoxy- or nitro-substituted, benzoyl, such as benzoyl, 4-chlorobenzoyl, 4-methoxybenzoyl or 4-nitrobenzoyl, lower alkoxycarbonyl, preferably lower alkoxycarbonyl that is branched in the 1-position of the lower alkyl radical or suitably substituted in the 1- or 2-position, for example tert-lower alkoxycarbonyl, such as tert-butoxycarbonyl, arylmethoxycarbonyl having one, two or three aryl radicals which are phenyl that is unsubstituted or mono- or poly-substituted, for example, by lower alkyl, especially tert-lower alkyl, such as tert-butyl, lower alkoxy, such as methoxy, hydroxy, halogen, such as chlorine, and/or by nitro, for example benzyloxycarbonyl, 4nitrobenzyloxycarbonyl, diphenylmethoxycarbonyl, 9-fluorenylmethoxycarbonyl or di(4methoxyphenyl)methoxycarbonyl, aroylmethoxycarbonyl wherein the aroyl group is preferably benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, 2-(tri-substituted silyl)-lower alkoxycarbonyl, for example 2-tri-lower alkylsilyl-lower alkoxycarbonyl, such as 2-trimethylsilylethoxycarbonyl or 2-(di-n-butyl-methyl-silyl)-ethoxycarbonyl, triarylsilyl-lower alkoxycarbonyl, for example 2-triphenylsilylethoxycarbonyl, or N,N-di-lower alkylformamidinyl, such as N,N-dimethylformamidinyl.

In an arylmethylamino group, for example a mono-, di- or especially tri-arylmethylamino group, the aryl radicals are especially unsubstituted or substituted phenyl radicals. Such groups are, for example, benzyl-, diphenylmethyl- or especially trityl-amino.

In an etherified mercaptoamino group the mercapto group is especially in the form of substituted arylthio or aryl-lower alkylthio, wherein aryl is, for example, phenyl that is unsubstituted or substituted, for example, by lower alkyl, such as methyl or tert-butyl, lower alkoxy, such as methoxy, halogen, such as chlorine, and/or by nitro, for example 4-nitrophenylthio.

In a 2-acyl-lower alk-1-enyl radical that can be used as an amino-protecting group, acyl is, for example, the corresponding radical of a lower alkanecarboxylic acid, of a benzoic acid that is unsubstituted or substituted, for example, by lower alkyl, such as methyl or tert-butyl, lower alkoxy, such as methoxy, halogen, such as chlorine, and/or by nitro, or especially of a carbonic acid semiester, such as a carbonic acid lower alkyl semiester. Corresponding protecting groups are especially 1-lower alkanoyl-lower alk-1-en-2-yl, for example 1-lower alkanoylprop-1-en-2-yl, such as 1-acetylprop-1-en-2-yl, or lower alkoxycarbonyl-lower alk-1-en-2-yl, for example lower alkoxycarbonylprop-1-en-2-yl, such as 1-ethoxycarbonylprop-1-en-2-yl.

A silylamino group is, for example, a tri-lower alkylsilylamino group, for example trimethylsilylamino or tert-butyl-dimethylsilylamino. The silicon atom of the silylamino group can also be substituted by only two lower alkyl groups, for example methyl groups, and by the amino group or carboxy group of a second molecule of a compound according to the invention. Compounds having such protecting groups can be prepared, for example, using the corresponding chlorosilanes, such as dimethylchlorosilane, as silylating agents.

An N-lower alkylpyrrolidinylidene group is preferably N-methylpyrrolidin-2-ylidene.

Preferred amino-protecting groups are lower alkoxycarbonyl, phenyl-lower alkoxycarbonyl, fluorenyl-lower alkoxycarbonyl, 2-lower alkanoyl-lower alk-1-en-2-yl and lower alkoxycarbonyl-lower alk-1-en-2-yl, with most preference being given to isobutyryl, benzoyl, phenoxyacetyl, 4-tert-butylphenoxyacetyl, N,N-dimethylformamidinyl and/or N-methylpyrrolidin-2-ylidene.

Primary amino (for example in the definition of $R_{b2}$, $R_{b3}$ and $R_{b5}$) contains preferably from 1 to 12, and especially from 1 to 6, carbon atoms, and secondary amino (for example in the definition of $R_{b2}$, $R_{b3}$ and $R_{b5}$) contains preferably from 2 to 12, and especially from 2 to 6, carbon atoms.

Some examples of alkyl, alkoxy, alkylthio, hydroxyalkyl and aminoalkyl containing preferably from 1 to 6 carbon atoms are methyl, ethyl and the isomers of propyl, butyl, pentyl, hexyl, heptyl, octyl, nonyl, decyl, undecyl and dodecyl, and corresponding alkoxy, alkylthio, hydroxyalkyl and aminoalkyl radicals. Alkyl, alkoxy, alkylthio, hydroxyalkyl and aminoalkyl contain especially from 1 to 4 carbon atoms. Preferred alkyl, alkoxy, alkylthio, hydroxyalkyl and aminoalkyl radicals are methyl, ethyl, n- and iso-propyl, n-, iso- and tert-butyl, methoxy, ethoxy, methylthio and ethylthio, aminomethyl, aminoethyl, hydroxymethyl and hydroxyethyl.

The primary amino and the secondary amino may be, for example, radicals of the formula $R_{a1}R_{a2}N$, wherein $R_{a1}$ is hydrogen or, independently, has the definition of $R_{a2}$, and $R_{a2}$ is $C_1$–$C_{20}$-, preferably $C_1$–$C_{12}$- and especially $C_1$–$C_6$-alkyl, $C_1$–$C_{20}$-, preferably $C_1$–$C_{12}$- and especially $C_1$–$C_6$aminoalkyl, $C_1$–$C_{20}$-, preferably $C_1$–$C_{12}$- and especially $C_1$–$C_6$-hydroxyalkyl; carboxyalkyl or carbalkoxyalkyl, the carbalkoxy group containing from 2 to 8 carbon atoms and the alkyl group from 1 to 6, preferably from 1 to 4, carbon atoms; $C_2$–$C_{20}$-, preferably $C_2$–$C_{12}$- and especially $C_2$–$C_6$alkenyl; phenyl, mono- or di-($C_1$–$C_4$alkyl or $C_1$–$C_4$alkoxy)phenyl, benzyl, mono- or di-($C_1$–$C_4$alkyl or $C_1$–$C_4$alkoxy)benzyl; or 1,2-, 1,3- or 1,4-imidazolyl-$C_1$–$C_6$alkyl, or $R_{a1}$ and $R_{a2}$ together are tetra- or penta-methylene, 3-oxa-1,5-pentylene, —CH$_2$—NR$_{a3}$—CH$_2$—CH$_2$— or —CH$_2$CH$_2$—NR$_{a3}$—CH$_2$CH$_2$—, wherein $R_{a3}$ is hydrogen or $C_1$–$C_4$alkyl. The amino group in aminoalkyl may be substituted by one or two $C_1$–$C_4$alkyl or $C_1$–$C_4$hydroxyalkyl groups. The hydroxy group in hydroxyalkyl may be etherified by $C_1$–$C_4$alkyl.

Examples of alkyl are given hereinbefore. Examples of aminoalkyl are aminomethyl, aminoethyl, 1-aminoprop-2-yl or -3-yl, 1-amino-but-2-yl or -3-yl or -4-yl, N-methyl- or N,N-dimethyl- or N-ethyl- or N,N-diethyl- or N-2-hydroxyethyl- or N,N-di-2-hydroxyethyl-aminomethyl or-aminoethyl or- aminopropyl or- aminobutyl. Examples of hydroxyalkyl are hydroxymethyl, 1-hydroxy-eth-2-yl, 1-hydroxy-prop-2- or -3-yl and 1-hydroxy-but-2-yl, -3-yl or -4-yl. Examples of carboxyalkyl are carboxymethyl, carboxyethyl, carboxypropyl and carboxybutyl, and examples of carbalkoxyalkyl are those carboxyalkyl groups esterified by methyl or by ethyl. Examples of alkenyl are allyl, but-1-en-3-yl or-4-yl, pent-3- or-4-en-1-yl or-2-yl, hex-3- or-4- or-2-yl. Examples of alkyl- and alkoxy-phenyl and alkyl- and alkoxy-benzyl are methylphenyl, dimethylphenyl, ethylphenyl, diethylphenyl, methylbenzyl, dimethylbenzyl, ethylbenzyl, diethylbenzyl, methoxyphenyl, dimethoxyphenyl, ethoxyphenyl, diethoxyphenyl, methoxybenzyl, dimethoxybenzyl, ethoxybenzyl and diethoxybenzyl. Examples of imidazolylalkyl in which the alkyl group preferably contains from 2 to 4 carbon atoms are 1,2-, 1,3- or 1,4-imidazolyl-ethyl or -n-propyl or -n-butyl. $R_{a3}$ is preferably hydrogen, methyl or ethyl.

Preferred examples of primary amino and secondary amino are methyl-, ethyl-, dimethyl-, diethyl-, allyl-, mono- or di-(1-hydroxy-eth-2-yl)-, phenyl- and benzyl-amino, acetylamino, isobutyrylamino and/or benzoylamino.

In a preferred form, $R_{b1}$ is hydrogen. In another preferred form, $R_{b5}$ is hydrogen. In a further preferred form, $R_{b2}$ and $R_{b3}$ are each independently of the other H, F, Cl, Br, OH, SH, $NH_2$, NHOH, $NHNH_2$, methylamino, dimethylamino, benzoylamino, isobutyrylamino, methoxy, ethoxy and methylthio.

Some examples of analogues of the purine series are, in addition to purine, xanthine, hypoxanthine, adenine, N-methyladenine, N-benzoyladenine, 2-methylthioadenine, 2-aminoadenine, 6-hydroxypurine, 2-amino-6-chloropurine, 2-amino-6-methylthiopurine, guanine, N-isobutyrylguanine. Especially preferred are adenine and guanine, and in a broader aspect of the invention 2-aminoadenine, or in a broader aspect of the invention the base-protected derivatives thereof.

If B in any one of formulae (Ii) to (Xi) and (Ii*) to (Xi*) is a pyrimidine radical or an analogue thereof, it is preferably a uracil, more preferably thymine or cytosine radical or an analogue thereof of formula XII, XIIa, XIIb or XIIc

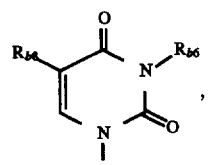
(XII)

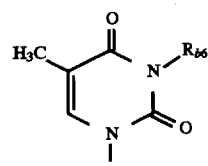
(XIIa)

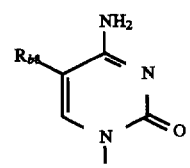
(XIIb)

or

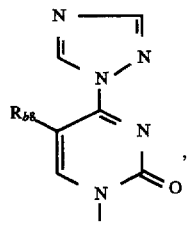
(XIIc)

wherein $R_{b6}$ is hydrogen or $C_1$–$C_4$alkyl and $R_{b8}$ is H, OH, SH, $NH_2$, $NHNH_2$, NHOH, NHO—$C_1$–$C_2$alkyl, —N=CH—N($C_1$–$C_{12}$alkyl)$_2$, F, Cl, Br, $C_1$–$C_{12}$alkyl, hydroxy-$C_1$–$C_{12}$alkyl, amino-$C_1$–$C_{12}$alkyl, $C_1$–$C_{12}$alkoxy, benzyloxy or $C_1$–$C_{12}$alkylthio, the hydroxy and amino groups being unsubstituted or substituted by a protecting group, or is phenyl, benzyl, primary amino having from 1 to 20 carbon atoms, secondary amino having from 2 to 30 carbon atoms, $C_1$–$C_{12}$alkenyl or $C_1$–$C_{12}$alkynyl, and the $NH_2$ group in formula XIIb is unsubstituted or substituted by $C_1$–$C_6$alkyl, benzoyl or by a protecting group, and the dihydro derivatives of the radicals of formulae XII, XIIa, XIIb and XIIc. $R_{b8}$ in formula XII is preferably hydrogen, $C_1$–$C_6$alkyl or $C_1$–$C_6$hydroxyalkyl, $C_2$–$C_6$alkenyl or $C_2$–$C_6$alkynyl, F, Cl, Br, $NH_2$, benzoylamino or mono- or di-$C_1$–$C_6$alkylamino. $R_{b8}$ in formulae XIIb and XIIc is preferably hydrogen, $C_1$–$C_6$alkyl or $C_1$–$C_6$-alkoxy or $C_1$–$C_6$hydroxyalkyl, $C_2$–$C_6$alkenyl or $C_2$–$C_6$alkynyl, F, Cl, Br, $NH_2$, benzoylamino or mono- or di-$C_1$–$C_6$ alkylamino.

$R_{b6}$ is preferably hydrogen or methyl. $R_{b8}$ in formula XII is preferably H, F, Cl, Br, $NH_2$, $NHCH_3$, $N(CH_3)_2$, $C_1$–$C_4$alkyl, $C_2$–$C_4$alkenyl or $C_2$–$C_4$alkyn-1-yl. $R_{b8}$ in formula XIIb and XIIc is preferably hydrogen, $C_1$–C4alkyl, especially methyl, $C_2$–C4alkenyl, especially vinyl, or $C_2$–$C_4$-alkyn-1-yl, especially 1-propyn-1-yl, or $NH_2$, $NHCH_3$ or $(CH_3)_2N$.

Some examples of pyrimidine analogues are uracil, thymine, cytosine, 5-fluorouracil, 5-chlorouracil, 5-bromouracil, dihydrouracil, 5-methylcytosine, 5-propynylthymine, 5-propynyluracil and 5-propynylcytosine, thymine, cytosine and 5-methylcytosine being most preferred.

Preferred are oligonucleotide derivatives which (in their nucleotide/nucleotide derivative sequence) comprise at least one of the following units (bivalent radicals) of the formulae given hereinafter, wherein B is a base radical as defined above, preferably of a base selected from thymine, uracil, 5-propynyluracil, cytosine, 5-methylcytosine, 5-propynylcytosine, adenine, 2-aminoadenine and guanine; Q is H, $OCH_3$, F, $O(CH_2CH_2O)_vCH_3$ wherein v is from 0 to 12, especially 1 or 3, $CH_2CH(CH_3)OCH_3$ or $CH_2CH(OH)CH_2OH$, or less preferably SH; and the other moieties have the meanings given behind the respective formula:

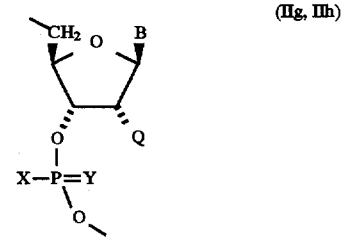
(IIg, IIh)

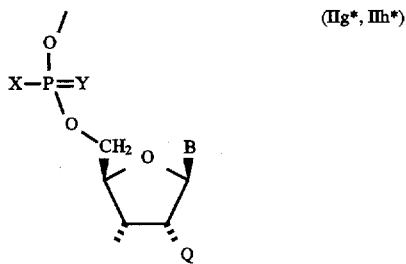

| Radical of formula | type | | |
|---|---|---|---|
| (IIg), (IIg*) | phosphorothioate | X=SH | Y=O or S |
| (IIh) (IIh*) | phosphodiester | X=OH | Y=O |

(the phosphodiesters IIh or IIh* being especially preferred), especially 2'-F derivatives, 2'-deoxy derivatives (Q=H) or 2'-(2-methoxy)ethoxy (2'-O-CH$_2$CH$_2$OCH$_3$) derivatives, the remaining internucleosidic bonds in the respective oligonucleotide derivative being of the phosphorothioate type; for synthesis see European Application EP 0 626 387 and International Application WO 92/20823; or oligonucleotide derivatives which comprise at least one of the following dimeric units (bivalent radicals) of the formulae given hereinafter, wherein each B is, independently of the other, a base radical as defined above, preferably of a base selected from thymine, uracil, 5-propynyluracil, cytosine, 5-methylcytosine, 5-propynylcytosine, adenine, 2-aminoadenine and guanine; any Q is, indepently of the other, H, OCH$_3$, F or O(CH$_2$CH$_2$O)$_v$CH$_3$ wherein v is from 0 to 12, especially 1; and the other moieties have the meanings given behind the respective formula:

| Radical of formula | type | X** | Y** |
|---|---|---|---|
| (VIe), VIe*) | amide | CH$_2$ | N(A) | wherein A is H, methyl or phenyl, preferably H; the remaining internucleosidic bonds in the respective oligonucleotide derivative being of the phosphorothioate type; for synthesis see International Application WO 95/20597 and International Application WO 92/20823;
or especially oligonucleotide derivatives, preferably oligo-2'-deoxynucleotide derivatives, where all internucleosidic bridges as of the phosphorothioate type and that have no sugar or base modification.

Preferred are also chimeric oligonucleotides which show, on the one hand, M regions of between 3 and 20 (preferably 5 to 15) modified building blocks (either with phosphodiester or with phosphorothioate backbone), especially with 2'-modification, especially 2'-(2-methoxy)ethoxy or 2'-F modified building blocks, which are in succeeding order; and, on the other hand, U regions of 4 to 20 2'-deoxy building blocks with phosphorothioate structure that are otherwise unmodified; preferably, the M and U regions can be in one of the following arrangements:

5'-M-U-M-3'

5'-M-U-3' or

5'-U-M-3'.

These chimeric oligonucleotides may be an own preferred group, as may be the other mentioned oligonucleotide derivatives.

Any —SH or —OH group bound to phosphorus, e.g. in phosphorothioate or phosphodiester internucleosidic bridges, is preferably present mainly in the ionized form under e.g. physiological conditions, that is as —O$^{(-)}$ or —S$^{(-)}$.

By the term "other chemotherapeutic agent" there is meant any chemotherapeutic agent except for antisense oligonucleotides or oligonucleotide derivatives targeted to raf-kinase that is or can be used in the treatment of tumor diseases, such as chemotherapeutics derived from the following classes:

(A) Alkylating agents, such as dacarbazine (DTIC-Dome); nitrogen mustards, such as mechlorethamine (Mustargen); ethyleneimine derivatives, e.g. triethylenethiophosphoramid (thio-tepa); procarbazine (Matulane); alkyl sulfonates such as busulfan (Myeleran); cyclophosphamide; 4-hydroxyperoxycyclophosphamide (4-HC); mafosfamide; ifosfamide; melphalan (Alkeran); chlorambucil (Leukeran); nitrosoureas such as cyclohexylnitrosourea (meCCNU; Carmustine, BCNU, BiCNU) or lomustine (CCNU, CeeNU), cis-platinum(II)-diaminedichloride (platinol or cisplatin); carboplatin (Paraplatin); preferably cross-linking chemotherapeutics, preferably bis-alkylating agents, especially nitrogen mustards, such as mechlorethamine (Mustargen); alkyl sulfonates such as busulfan (Myeleran); cyclophosphamide; melphalan (Alkeran); chlorambucil (Leukeran); cis-platinum(II)-diaminedichloride (platinol or cisplatin) or carboplatin (Paraplatin); or compounds that form cross-links via ionic bonds, such as ethyleneimine derivatives, e.g. triethylenethiophosphoramid (thio-tepa) (forms ionic cross-links);

(B) antitumor antibiotics, preferably selected from the group comprising bleomycine (Blenoxane); anthracyclines, such as daunomycin, dactinomycin (Cosmegen), daunorubicin (Cerubidine), doxorubicin (Adriamycin, Rubex), epirubicin, esorubicin, idarubicin (Idamycin), plicamycin (Mithracin, formerly called Mithramycin) and preferably cross-linking (bis-alkylating) antitumor antibiotics, such as mitomycin C (Mitomycin, Mutamycin);

(C) antimetabolites, for example folic acid analogues such as methotrexate (Folex, Mexate) or trimetrexate; purine nucleoside analogues such as Cladribine (Leustatin; 2-chloro-2'-deoxy-β-D-adenosine), 6-mercaptopurine (Mercaptopurine, Purinethol, 6-MP), pentostatin (Nipent) or 6-thioguanine (6-TG, Tabloid); pyrimidine analogues such as 5-fluorouracil (Fluoruracil, 5-FU), 5-fluorodeoxyuridine (Floxuridine, FUDR), cytosine arabinoside (ara-C, cytarabine, Cytosar-U or Tarabine PFS), fludarabin phosphate (Fludara) or 5-azacytidine; hydroxyurea (Hydrea); or polyamine biosynthesis inhibitors, especially ornithine decarboxylase inhibitors or S-adenosylmethionine decarboxylase inhibitors, for example those mentioned in EP 0 456 133, especially 4-amidino-1-indanon-2'-amidinohydrazone;

(D) plant alkaloids, preferably vinca alkaloids, such as vinblastine (Velban), vincristine (Oncovin) or vindesine; epipodophyllotoxins, such as etoposide (VP-16, VePesid) or teniposide (VM-26, Vumon);

(E) hormonal agents and antagonists, preferably adrenocorticoids, such as prednisone (Deltasone) or dexamethasone (Decadron); progestines such as hydroxyprogesterone (Prodox), megestrol acetate (Megace) or medroxyprogesterone (Provera, Depo-Provera); androgens such as testosterone or fluoxymesterone (Halotestin); estrogens such as diethylstilbestrol (DES), estradiol or chlorotriansiene (Tace); synthetic analogues of LHRH, such as goserelin (Zoladex); synthetic analogues of LH-releasing hormone, such as leuprolide (Lupron, Lupron Depot); anti-androgens such as flutamide (Eulexin); anti-estrogens such as tamoxifen; aromatase inhibitors such as aminogluthetimide (Cytadren), lentaron (Formestane, 4-hydroxy-4-androsten-3,17-dione) (see EP 0 162 510), fadrozole (5-(p-cyanophenyl)-5,6,7,8-tetrahydroimidazo [1,5-a]pyridin, see EP 0 437 415 and EP 0 165 904), letrozole (4,4'-(1H-1,2,4-triazol-1-yl-methylen)-bis-benzonitrile, see U.S. Pat. No. 4,976, 672), 4-(α-(4-cyanophenyl)-α-fluoro-1-(1,2,4-triazolyl)methyl)-benzonitrile (see EP 0 490 816) or 4-(α-(4-cyanophenyl)-(2-tetrazolyl)methyl)-benzonitrile (see EP 0 408 509); adrenal cyctooxic agents, such as mitotane (Lysodren); somatostatine analogues, such as octreotide (Sandostatin); or 5α-reductase inhibitors, such as N-(1-cyano-1-methyl-ethyl)-4-aza-3-oxo-5α-androst-1-en-17β-carboxamid (see EP 0 538 192);

(F) biological response modifiers, preferably lymphokines, such as aldesleukin (human recombinant IL-2, Proleukin); or interferons, such as interferon-α (Intron-A, Roferon) or interferon "$B_1B_2B_3D_4$" (see EP 0 205 404);

(G) inhibitors of protein tyrosine kinases and/or serine/threonine kinases other than ODNs, such as N-{5-[4-methyl-piperazino-methyl)-benzoylamido]-2-methyl-phenyl}-4-(3-pyridyl)-2-pyrimidine (see EP 0 546 409), N-(3-chlorophenyl)-4-(2-(3-hydroxy)-propyl-amino-4-pyridyl)-2pyridyl-2-pyrimidinamin (see EP 0 606 046), N-benzoyl-staurosporine (see EP 0 296 110), 4,5-bis-(anilino)-phthalimide (see EP 0 516 588), N-(5-benzoylamido-2-methyl-phenyl)-4-(3-pyridyl)-2-pyridinamin (see EP 0 564 409) or 4-(m-chloranilino)-5,6-dimethyl-7H-pyrrolo[2,3-d]pyrimidin (see EP 0 682 027);

(H) antisense oligonucleotides or oligonucleotide derivatives targeted to other targets than PKC, such as those targeted to SAMDC (PCT application WO WO 96/05298) but except for those targeted to raf-kinase (see International Application WO 95/32987); or (I) miscellaneous agents or agents with other or unknown mechanism of action, preferably S-triazine derivatives, such as altrematine (Hexalen); enzymes, such as asparaginase (Elspar); methylhydrazine derivatives, such as dacarbazine and procarbazine; matrix metalloproteinase inhibitors, such as (Case 4-19421) hexamethylmelamine, pentamethylmelamine; anthraquinones such as mitoxantrone (Novantrone); mitotic spindle poisons such as paclitaxel (Taxol); streptozocin (Zanosar); estracyt (estramustine); amsacrine; differentiating agents, such as all-trans retinoic acid (TRA); immunomodulators, such as levamisole (ergamisol); vaccines, e.g. anti-melanoma vaccines (see EP 0 674 097); or antibodies with antitumor activity, such as recombinant human immunoglobulins directed at melanoma antigen (see EP 0 640 131) or antibodies for active immunotherapy of melanoma (see EP 0 428 485).

More preferred is any of the above-mentioned chemotherapeutic agents except for oligonucleotide derivative targeted at PKC, adriamycin (doxorubicin) and cyclophosphamide, preferably alone, or more preferably alone or in any combination.

Especially preferred are the chemotherapeutic agents mentioned above under (A) as cross-linking chemotherapeutics, preferably bis-alkylating agents, especially nitrogen mustards, such as mechlorethamine (Mustargen); alkyl sulfonates such as busulfan (Myeleran); cyclophosphamide; melphalan (Alkeran); chlorambucil (Leukeran); cis-platinum(II)-diaminedichloride (platinol or cisplatin) or carboplatin (Paraplatin); or compounds that form cross-links via ionic bonds, such as ethyleneimine derivatives, e.g. triethylenethiophosphoramid (thio-tepa) (forms ionic cross-links); chemotherapeutic agents mentioned under (B) as cross-linking (bis-alkylating) antitumor antibiotics, such as mitomycin C (Mitomycin, Mutamycin); or vinca alkaloids, such as vinblastine (Velban), vincristine (Oncovin) or vindesine.

Preferably, the term "other chemotherapeutic agent" relates to a standard chemotherapeutic agent as mentioned before that is already used clinically, or in a less preferred sense also to a chemotherapeutic agent that is already being tested clinically.

Most preferred is one or more of the chemotherapeutics selected from the group comprising cisplatin, mitomycine and vinblastine.

By the term "proliferative disease that can be trated by administration of an oligonucleotide or oligonucleotide derivative targeted to PKC" there is meant any disease that responds to such compounds; especially, by a disease that "responds to modulation of PKC activity" there is preferably meant a proliferative disease selected from hyperproliferative conditions such as cancers, tumors, hyperplasias, fibrosis (espeically pulmonary fibrosis, but also other kinds of fibrosis, such as renal fibrosis), angiogenesis, psoriasis, atherosclerosis and smooth muscle cell proliferation in the blood vessels, such as stenosis or restenosis following angioplasty.

Most preferably, the disease is one selected from cancer types which have been very difficult to treat or even practically unaffected by therapy with standard chemotherapeutics, such as small cell lung carcinoma, large cell lung carcinoma, melanoma, prostate carcinoma or further also lymphoma. Most preferably, any of the aforementioned proliferative diseases that can be treated by inhibition of human PKC-α activity is meant. Treatment of prostate carcinomas, lung carcinomas, especially large lung cell carcinomas, or breast cancer is especially preferred.

By the term "quantity which is jointly therapeutically effective against proliferative diseases that can be treated by an oligonucleotide or oligonucleotide derivative targeted to PKC, especially PKC-α, or that preferably depend on PKC, especially PKC-α, activity" there is preferably meant any quantity of the components of the combinations that, in the combination, is diminishing proliferation of cells responsible for any of the mentioned proliferative diseases (e.g. diminished tumor growth) or, preferably, even causing regression, more preferably even the partial or complete disappearance, of such cells (e.g. tumor regression, preferably cure). The term "that depend on PKC-activity" is preferably intended to mean any proliferative diseases that can be influenced, especially alleviated, by hybridization of a PKC-specific (especially PKC-α-specific) ODN to its target, as described hereinbefore and hereinafter.

By the term "a product which comprises
a) at least one oligonucleotide or oligonucleotide derivative (ODN) targeted to nucleic acids encoding (especially human) PKC, especially PKC-α, and
b) at least one other chemotherapeutic agent where any component a) and/or b).can also be present in the form of a pharmaceutically acceptable salt, if at least one salt-forming group is present, in the presence or absence of one or more pharmaceutically acceptable carrier materials, as a combination preparation for simultaneous or chronologically staggered use within a period of time which is small enough for the active compounds both of component a) and of component b) to mutually enhance antiproliferative activity in the patient, for treating a proliferative disease which responds to such active compounds", there is preferably meant especially a "kit of parts" in the sense that the effective components a) and b) of the combination can be dosed independently or by use of different fixed combinations with distinguished amounts of any components a) and b) at different time points.

The parts of the kit of parts can then be administered simultaneously or chronologically staggered, that is at different time points and with equal or different time intervals for any part of the kit of parts, with the condition that the time intervals are chosen such that the effect on the proliferative disease in the combined use of the parts is larger than the effect which would be obtained by use of only any one of component a) and b), that is, stronger inhibition of proliferation or, preferably, stronger regression or even cure of the proliferative disease is found than when the same dose of only one of components a) and b) is administered alone in the same dose. That is meant by the term "to mutually enhance antiproliferative activity against proliferating cells, especially in a patient"; preferably, there is meant a mutual enhancing of the effect of the components a) and b), especially a synergism and/or the causing of regression of the proliferating cells, up to and including their complete destruction, and especially a strong synergism between components a) and b).

By the term "proliferating cells", preferably abnormally proliferating cells are meant.

Preferred are combinations which show enhanced antiproliferative activity when compared with the single components alone, especially combinations that show synergism (synergistic combinations) or combinations that lead to regression of proliferative tissues and/or cure from proliferative diseases.

The term "synergism" is standing for an effect that is stronger than additive, that is, a stronger effect of the combination of any component a) with any component b) than could be reached by the factor of diminution of proliferation obtained from mere multiplication of the factor of diminution of proliferation for any component a) alone or any component b) alone when compared to a control without treatment when each a) and b) as such, whether alone or in combination, is administered in the same dose as in the single treatment without combination (which does not mean that the dose of a) and b) must be identical, although this may also be the case). As theoretical example for mere illustration, if a component a) alone gives a growth of tumor cells that is diminished by a factor of 2 in comparison to a control without any treatment and a component b) alone gives a diminution of growth by a factor of 1.5, then an additive effect would be one where, by combined use of component a) and component b), a 3-fold diminution of growth would be found (multiplication of 2 with 1.5). A synergistic effect would be present if a more than 3-fold diminution of proliferation is found.

By the term "quantity, which is jointly (therapeutically) effective for treating a proliferative disease that can be treated by administration of an oligonucleotide or oligonucleotide derivative targeted to (especially human) PKC, especially PKC-α (preferably that can be treated by modulation of (especially human) PKC, especially PKC-α, activity)", there is preferably meant a quantity of component a) and component b) which is effective in the treatment of one of the proliferative diseases mentioned above, that is, which leads to diminished proliferation or preferably even to regression of the proliferating cells (e.g. tumor regression) or even to cure from the proliferative disease. This term not only comprises combinations of any component a) and b) where a) and b) are dosed in such a manner as to be antiproliferatively effective already without combination, but also doses of any such component which alone would show no or only marginal effect but which in combination leads to clearly antiproliferative effects, that is to diminished proliferation or preferably even to regression of the proliferating cells or even to cure from the proliferative disease. In addition, here the term "combination" is not only used to describe fixed combinations of the components, but also any combination of components a) and b) for simultaneous or chronologically staggered use within a period of time which is small enough for the active compounds both of component a) and of component b) to mutually enhance antiproliferative activity, e.g. in a patient.

The term "one or more pharmaceutically acceptable carrier materials" is explained below in the definition of pharmaceutical preparations.

It is to be understood that the invention relates also to any use of combinations of a component a) and a component b), as defined above and below, in a method of inhibiting hyperproliferation of cells comprising contacting hyperproliferating cells with a pharmaceutical preparation or product in the sense of a kit of parts, especially a method of treating a proliferative disease comprising contacting a subject, cells, tissues or a body fluid of said subject, suspected of having a hyperproliferative disease. This includes especially the treatment of e.g. cells outside the body with the intent to replace hyperproliferating cells in the body of a subject with hyperproliferating cells by normal cells; for example, blood cells of the immune system may be taken from a subject, treated outside the body with a component a) and a component b) to select for non-hyperproliferative cells, the stem cells and the remaining blood cells of the immune system may be destroyed in the subject e.g. by irradiation or chemotherapy and then the selected normal cells may be reimplanted into the subject, e.g. by injection etc. The methods to be employed in such kinds of treatment are known to the person having skill in the art.

Any of the references mentioned within this specification is incorporated by reference, especially those passages marked as preferred herein, especially International Application WO 95/32987, WO 93/19203 or WO 95/02069.

Provided that salt-forming groups are present, the ODN as well as the other chemotherapeutic(s) may also be present in the form of salts.

Salts of oligonucleotides or oligonucleotide derivatives are especially acid addition salts, salts with bases or, when several salt-forming groups are present, optionally also mixed salts or internal salts.

Salts are especially the pharmaceutically acceptable, e.g. substantially non-toxic, salts of oligonucleotides or oligonucleotide derivatives as specified above and below.

Such salts are formed, for example, from the oligonucleotides or oligonucleotide derivatives having an acidic group, for example a carboxy, phosphodiester or phosphorothioate group, and are, for example, their salts with suitable bases, such as non-toxic metal salts derived from metals of groups Ia, Ib, IIa and IIb of the Periodic Table of Elements, especially suitable alkali metal salts, for example lithium, sodium or potassium salts, or alkaline earth metal salts, for example magnesium or calcium salts, furthermore zinc or ammonium salts, also those salts that are formed with organic amines, such as unsubstituted or hydroxy-substituted mono-, di- or tri-alkylamines, especially mono-, di- or tri-lower alkylamines, or with quaternary ammonium compounds, for example with N-methyl-N-ethylamine, diethylamine, triethylamine, mono-, bis- or tris-(2-hydroxy-lower alkyl)amines, such as mono-, bis- or tris-(2-hydroxyethyl)amine, 2-hydroxy-tert-butylamine or tris (hydroxymethyl)methylamine, N,N-di-lower alkyl-N-(hydroxy-lower alkyl)-amines, such as N,N-dimethyl-N-(2-hydroxyethyl)-amine or trio-(2-hydroxyethyl)-amine, or N-methyl-D-glucamine, or quaternary ammonium salts, such as tetrabutylammonium salts. The oligonucleotides and their derivatives having a basic group, for example an amino or imino group, can form acid addition salts, for example with inorganic acids, for example a hydrohalic acid, such as hydrochloric acid, sulfuric acid or phosphoric acid, or with organic carboxylic, sulfonic, sulfo or phospho acids or N-substituted sulfamic acids, such as, for example, acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, also with amino acids, for example, α-amino acids, and also with methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, 2- or 3-phosphoglycerate, glucose-6-phosphate, N-cyclohexylsulfamic acid (with formation of the cyclamates) or with other acidic organic compounds, such as ascorbic acid. Compounds having acidic and basic groups can also form internal salts. If more than one salt-forming group is present, it is also possible that mixed salts are present. Corresponding salts can be formed from other chemotherapeutic agents provided that salt-forming groups are present therein.

For the purpose of isolation or purification, it is also possible to use pharmaceutically unacceptable salts, for example picrate or perchlorate salts.

The terms "oligonucleotides", "oligonucleotide derivatives", "compounds" and "salts" also expressly include individual compounds or individual salts.

The antitumor activity of SEQ-ID NO: 1-ODN as single agents is tested against various human tumors transplanted subcutaneously into nude mice. The human tumors tested are A549 lung carcinomas (ATCC No. CCL 185), T24 bladder carcinomas (ATCC No. HTB 4), MDA-MB-231 breast carcinomas (ATCC HTB 26) and Colo 205 colon carcinomas (ATCC CCL 222). The ODN is given once daily by the intravenous route of application when the tumor reaches a mean volume of approximately 100 mm$^3$ throughout the experiments. In a standard experiment drug application is started at day 10 and continued until the end of the experiment at day 30 at doses of 6, 0.6, 0.06, 0.006 mg/kg. In all tumor types tested, the SEQ-ID NO: 1-ODN exhibits significant antitumor activity in the dose range of 0.06–6.0 mg/kg. The most sensitive tumor is A549 lung carcinoma (significant activity at 0.006 mg/kg), followed by T24 bladder and MDA-MB-231 breast carcinoma and Colo 205 colon carcinoma, transplanted into nude mice (significant activity at 6 mg/kg). The antitumor effects of the SEQ-ID NO: 1-ODN are sequence-specific since scrambled control ODNs do not show antitumor effects. A scrambled phosphothioate control (same base composition, but in totally different sequence) ODN to SEQ-ID NO: 1-ODN did not show antitumor activity in T24 bladder and A549 lung carcinomas, indicating that the antitumor effects of the SEQ-ID NO: 1-ODN in vivo are specific and sequence-dependent.

The effects of combinations of a component a) (PKC-targeted ODN) with a component b) (other chemotherapeutic agent) can preferably be shown in analogy to the methods shown below in the passage providing examples, preferably with the animals, tumor cell lines, conditions and combinations mentioned there.

As can be understood from the present text, the term "combination" in the following paragraphs which describe more specific and preferred variants of the present invention is intended to refer to (i) combination preparations comprising at least one oligonucleotide or oligonucleotide derivative (ODN) targeted to nucleic acids encoding (especially human) PKC, especially PKC-α, with at least one other chemotherapeutic agent; or (ii) a method for treating a proliferative disease that can be treated by administration of an oligonucleotide or oligonucleotide derivative targeted to PKC, especially PKC-α, especially where the disease responds to modulation of PKC, especially PKC-α, activity, where a) at least one oligonucleotide or oligonucleotide derivative (ODN) targeted to nucleic acids encoding (especially human) PKC and capable of modulating (especially human) PKC, especially PKC-α expression and b) at least one other chemotherapeutic agent are administered to a mammal in combination in a quantity which is jointly therapeutically effective against proliferative diseases that can be treated by an oligonucleotide or oligonucleotide derivative targeted to PKC, especially PKC-α, or that preferably depend on PKC, especially PKC-α, activity in order to treat them, or (iii) a product which comprises
  a) at least one oligonucleotide or oligonucleotide derivative (ODN) targeted to nucleic acids encoding (especially human) PKC, especially PKC-α, and
  b) at least one other chemotherapeutic agent in the presence or absence of one or more pharmaceutically acceptable carrier materials, as a combination preparation for simultaneous or chronologically staggered use within a period of time which is small enough for the active compounds both of component a) and of component b) to mutually enhance antiproliferative activity against proliferating cells, especially in a patient, for treating a proliferative disease which responds to such active compounds; or (iv) a pharmaceutical preparation which comprises a quantity, which is jointly effective for treating a proliferative disease that can be treated by administration of an oligonucleotide or oligonucleotide derivative targeted to PKC, especially PKC-α (preferably that can be treated by modulation of (especially human) PKC, especially PKC-α, activity), of
  a) at least one oligonucleotide or oligonucleotide derivative (ODN) targeted to nucleic acids encoding (especially human) PKC, especially PKC-α, and
  b) at least one other chemotherapeutic agent, with one or more pharmaceutically acceptable carrier materials; or (v) the use of a combination of
  a) at least one oligonucleotide or oligonucleotide derivative (ODN) targeted to nucleic acids encoding (especially human) PKC, especially PKC-α, and
  b) at least one other chemotherapeutic agent, for producing pharmaceutical preparations for use as compositions against a proliferative disease that can be treated by application of an oligonucleotide or oligonucleotide derivative targeted to PKC, especially human PKC-α (preferably a proliferative disease that can be treated by modulation of PKC activity);

or any combination of these subjects of the invention, as far as permissible under the respective patent laws; or the more specific and preferred variants thereof as given below;

where any component a) and/or b) can also be present in the form of a pharmaceutically acceptable salt, if at least one salt-forming group is present.

Within the following groups of more preferred embodiments of the invention, more general definitions may be replaced by more specific definitions in accordance with those given above or (especially with regard to definition of pharmaceutical compositions and methods of use) below.

Preferred is a combination (preferably synergistic and/or causing regression up to and including complete cure) of a) at least one oligonucleotide derivative (ODN) targeted to nucleic acids encoding human PKC, especially PKC-α, the oligonucleotide derivative preferably being one that corresponds to an oligonucleotide derivative as published in PCT application WO 93/19203 or WO 95/02069, especially in the examples thereof, more preferably an oligonucleotide derivative that corresponds to the following sequence:

5'- GTT CTC GCT GGT GAG TTT CA -3'      SEQ.-ID NO: 1, (or also a version thereof which is terminally shortened on one or both ends, e.g. with 15 to 19 building blocks, most especially the derivative as such)
which is preferably present as an oligonucleotide derivative which (in its nucleotide/nucleotide derivative sequence) comprises at least one of the following units of the formulae given hereinafter, wherein B is a base radical as defined above, preferably of a base selected from thymine, uracil, 5-propynyluracil, cytosine, 5-methylcytosine, 5-propynylcytosine, adenine, 2-aminoadenine and guanine; Q is H, $OCH_3$, F, $O(CH_2CH_2O)_vCH_3$ wherein v is from 0 to 12, especially 1 or 3, $CH_2CH(CH_3)OCH_3$ or $CH_2CH(OH)CH_2OH$, or less preferably SH; and the other moieties have the meanings given behind the respective formula:

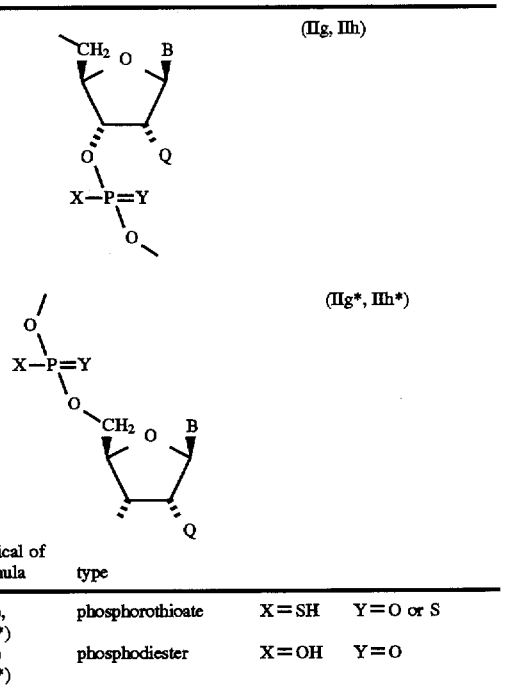

| Radical of formula | type | | |
|---|---|---|---|
| (IIg), (IIg*) | phosphorothioate | X=SH | Y=O or S |
| (IIh) (IIh*) | phosphodiester | X=OH | Y=O |

(the phosphodiesters IIh or IIh* being especially preferred), especially 2'-deoxy derivatives (Q=H) or 2'-(2-methoxy)ethoxy (2'-O—$CH_2CH_2OCH_3$) derivatives, the remaining internucleosidic bonds in the respective oligonucleotide derivative being of the phosphorothioate type; for synthesis see European Application EP 0 626 387 and International Application WO 92/20823; or as oligonucleotide derivative which comprises at least one of the following dimeric units (bivalent radicals) of the formulae given hereinafter, wherein each B is, independently of the other, a base radical as defined above, preferably of a base selected from thymine, uracil, 5-propynyluracil, cytosine, 5-methylcytosine, 5-propynylcytosine, adenine, 2-aminoadenine and guanine; any Q is, indepently of the other, H, $OCH_3$, F or $O(CH_2CH_2O)_vCH_3$ wherein v is from 0 to 12, especially 1; and the other moieties have the meanings given behind the respective formula:

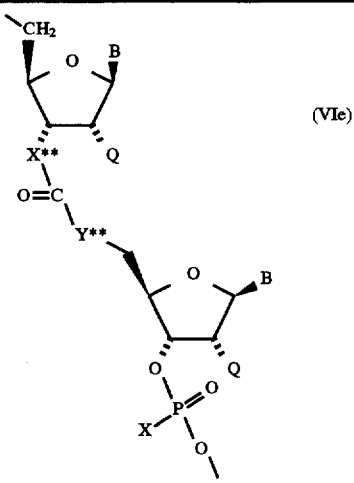

(VIe)

| Radical of formula | type | X** | Y** |
|---|---|---|---|
| (VIe), (VIe*) | amide | CH₂ | N(A) | wherein A is H, methyl or phenyl, preferably H; the remaining internucleosidic bonds in the respective oligonucleotide derivative being of the phosphorothioate type; for synthesis see International Application WO 95/20597 and International Application WO 92/20823; or (alternatively or in addition) as oligonucleotide derivative which is present in the form of a chimeric oligonucleotide which shows, on the one hand, M regions of between 3 and 20 (preferably 5 to 15) modified building blocks (either with phosphodiester or with phosphorothioate backbone), especially 2'-(2-methoxy) ethoxy (more preferred) or 2'-F modified building blocks, which are in succeeding order; and, on the other hand, U regions of 4 to 20 2'-deoxy building blocks with phosphorothioate structure that are otherwise unmodified; preferably, the M and U regions being in one of the following arrangements:

5'-M-U-M-3'

5'-M-U-3' or

5'-U-M-3';

or especially oligonucleotide derivatives, preferably oligo-2'-deoxynucleotide derivatives, where all internucleosidic bridges as of the phosphorothioate type and that have no sugar or base modification; and b) at least one other chemotherapeutic agent, preferably selected from (A) alkylating agents, such as dacarbazine (DTIC-Dome); nitrogen mustards, such as mechlorethamine (Mustargen); ethyleneimine derivatives, e.g. triethylenethiophosphoramid (thio-tepa); procarbazine (Matulane); alkyl sulfonates such as busulfan (Myeleran); cyclophosphamide; 4-hydroxyperoxycyclophosphamide (4-HC); mafosfamide; ifosfamide; melphalan (Alkeran); chlorambucil (Leukeran); nitrosoureas such as cyclohexylnitrosourea (meCCNU; Carmustine, BCNU, BiCNU) or lomustine (CCNU, CeeNU), cis-platinum(II)-diaminedichloride (platinol or cisplatin); carboplatin (Paraplatin); preferably cross-linking chemotherapeutics, preferably bis-alkylating agents, especially nitrogen mustards, such as mechlorethamine (Mustargen); alkyl sulfonates such as busulfan (Myeleran); cyclophosphamide; melphalan (Alkeran); chlorambucil (Leukeran); cis-platinum (II)-diaminedichloride (platinol or cisplatin) or carboplatin (Paraplatin); or compounds that form cross-links via ionic bonds, such as ethyleneimine derivatives, e.g. triethylenethiophosphoramid (thiotepa) (forms ionic cross-links);

(B) antitumor antibiotics, preferably selected from the group comprising bleomycine (Blenoxane); anthracyclines, such as daunomycin, dactinomycin (Cosmegen), daunorubicin (Cerubidine), doxorubicin (Adriamycin, Rubex), epirubicin, esorubicin, idarubicin (Idamycin), plicamycin (Mithracin, formerly called Mithramycin) and preferably cross-linking (bis-alkylating) antitumor antibiotics, such as mitomycin C (Mitomycin, Mutamycin);

(C) antimetabolites, for example folic acid analogues such as methotrexate (Folex, Mexate) or trimetrexate; purine nucleoside analogues such as Cladribine (Leustatin; 2-chloro-2'-deoxy-β-D-adenosine), 6-mercaptopurine (Mercaptopurine, Purinethol, 6-MP), pentostatin (Nipent) or 6-thioguanine (6-TG, Tabloid); pyrimidine analogues such as 5-fluorouracil (Fluoruracil, 5-FU), 5-fluorodeoxyuridine (Floxuridine, FUDR), cytosine arabinoside (ara-C, cytarabine, Cytosar-U or Tarabine PFS), fludarabin phosphate (Fludara) or 5-azacytidine; hydroxyurea (Hydrea); or polyamine biosynthesis inhibitors, especially ornithine decarboxylase inhibitors or S-adenosylmethionine decarboxylase inhibitors, for example those mentioned in EP 0 456 133, especially 4-amidino-1-indanon-2'-amidinohydrazone;

(D) plant alkaloids, preferably vinca alkaloids, such as vinblastine (Velban), vincristine (Oncovin) or vindesine; epipodophyllotoxins, such as etoposide (VP-16, VePesid) or teniposide (VM-26, Vumon);

(E) hormonal agents and antagonists, preferably adrenocorticoids, such as prednisone (Deltasone) or dexamethasone (Decadron); progestines such as hydroxyprogesterone (Prodox), megestrol acetate (Megace) or medroxyprogesterone (Provera, Depo-Provera); androgens such as testosterone or fluoxymesterone (Halotestin); estrogens such as diethylstilbestrol (DES), estradiol or chlorotriansiene (Tace); synthetic analogues of LHRH, such as goserelin (Zoladex); synthetic analogues of LH-releasing hormone, such as leuprolide (Lupron, Lupron Depot); anti-androgens such as flutamide (Eulexin); anti-estrogens such as tamoxifen; aromatase inhibitors such as aminogluthetimide (Cytadren), lentaron (Formestane, 4-hydroxy-4-androsten-3,17-dione) (see EP 0 162 510), fadrozole (5-(p-cyanophenyl)-5,6,7,8-tetrahydroimidazo [1,5-a]pyridin, see EP 0 437 415 and EP 0 165 904), letrozole (4,4'-(1H-1,2,4-triazol-1-yl-methylen)-bis-benzonitrile, see U.S. Pat. No. 4,976,672), 4-(α-(4-cyanophenyl)-α-fluoro-1-(1,2,4-triazolyl)methyl)-benzonitrile (see EP 0 490 816) or 4-(α-(4-cyanophenyl)-(2-tetrazolyl)methyl)-benzonitrile (see EP 0 408 509); adrenal cyctooxic agents, such as mitotane (Lysodren); somatostatine analogues, such as octreotide (Sandostatin); or 5α-reductase inhibitors, such as N-(1-cyano-1-methyl-ethyl)-4-aza-3-oxo-5α-androst-1-en-17β-carboxamid (see EP 0 538 192);

(F) biological response modifiers, preferably lymphokines, such as aldesleukin (human recombinant IL-2, Proleukin); or interferons, such as interferon-α (Intron-A, Roferon) or interferon "B₁B₂B₃B₄" (see EP 0 205 404);

(G) inhibitors of protein tyrosine kinases and/or serine/threonine kinases other than ODNs, such as N-{5-[4-methyl-piperazino-methyl)-benzoylamido]-2-methyl-phenyl}-4-(3-pyridyl)-2-pyrimidine (see EP 0 546 409), N-(3-chlorophenyl)-4-(2-(3-hydroxy)-propyl-amino-4-pyridyl)-2-pyrimidinamin (see EP 0 606 046), N-benzoyl-staurosporine (see EP 0 296 110), 4,5-bis-(anilino)-phthalimide (see EP 0 516 588), N-(5-benzoylamido-2-methyl-phenyl)-4-(3-pyridyl)-2-pyridinamin (see EP 0 564 409) or 4-(m-chloranilino)-5,6-dimethyl-7H-pyrrolo[2,3-d]pyrimidin (see EP 0 682 027);

(H) antisense oligonucleotides or oligonucleotide derivatives targeted to other targets than PKC, such as those targeted to SAMDC (PCT application WO 96/05298) but except for thos targeted to raf kinase (International Application WO 95/32987); and (I) miscellaneous agents or agents with other or unknown mechanism of action, preferably S-triazine derivatives, such as altrematine (Hexalen); enzymes, such as asparaginase (Elspar); methylhydrazine derivatives, such as dacarbazine and procarbazine; matrix metalloproteinase inhibitors, such as (Case 4-19421) hexamethylmelamine, pentamethylmelamine; anthraquinones such as mitoxantrone (Novantrone); mitotic spindle poisons such as paclitaxel (Taxol); streptozocin (Zanosar); estracyt (estramustine); amsacrine; differentiating agents, such as all-trans retinoic acid (TRA); immunomodulators, such as levamisole (ergamisol); vaccines, e.g. anti-melanoma vaccines (see EP 0 674 097); or antibodies with antitumor activity, such as recombinant human immunoglobulins directed at melanoma antigen (see EP 0 640 131) or antibodies for active immunotherapy of melanoma (see EP 0 428 485), more preferably selected from the chemotherapeutics mentioned above under (A) as cross-linking chemotherapeutics, preferably bis-alkylating agents, especially nitrogen mustards, such as mechlorethamine (Mustargen); alkyl sulfonates such as busulfan (Myeleran); cyclophosphamide; melphalan (Alkeran); chlorambucil (Leukeran); cis-platinum(II)-diaminedichloride (platinol or cisplatin) or carboplatin (Paraplatin); or compounds that form cross-links via ionic bonds, such as ethyleneimine derivatives, e.g. triethylenethiophosphoramid (thio-tepa) (forms ionic cross-links); chemotherapeutic agents mentioned under (B) as cross-linking (bis-alkylating) antitumor antibiotics, such as mitomycin C (Mitomycin, Mutamycin); or vinca alkaloids, such as vinblastine (Velban), vincristine (Oncovin) or vindesine; most preferably a standard chemotherapeutic agent selected from the group comprising cisplatin, mitomycine and vinblastine;

where any component a) and/or b) can also be present in the form of a pharmaceutically acceptable salt, if at least one salt-forming group is present.

Preferred is especially a combination of a) at least one oligonucleotide derivative (ODN) targeted to nucleic acids encoding human PKC-α, and that corresponds to the following sequence:

5'-GTT CTC GCT GGT GAG TTT CA-3'   SEQ. ID NO:1, (or also a version thereof which is terminally shortened on one or both ends, e.g. with 15 to 19 building blocks, most especially the derivative as such)

which is preferably present as an oligonucleotide (especially oligo-2'-deoxynucleotide) derivative which (in its nucleotide/nucleotide derivative sequence) comprises at least one of the following units of the formulae given hereinafter, wherein B is a base radical as defined above, preferably of a base selected from thymine, uracil, 5-propynyluracil, cytosine, 5-methylcytosine, 5-propynylcytosine, adenine, 2-aminoadenine and guanine; Q is H, OCH₃, F, O(CH₂CH₂O)ᵥCH₃ wherein v is from 0 to 12, especially 1 or 3, CH₂CH(CH₃)OCH₃ or CH₂CH(OH)CH₂OH; and the other moieties have the meanings given behind the respective formula:

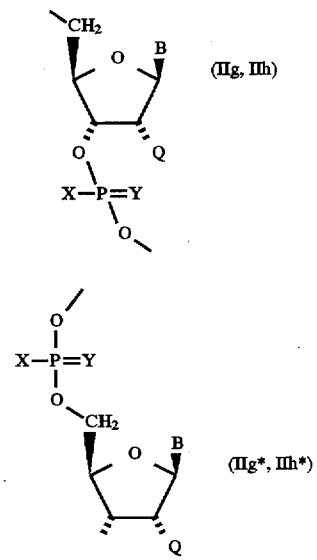

| Radical of formula | type | | |
|---|---|---|---|
| (IIg), (IIg*) | phosphorothioate | X = SH | Y = O or S |
| (IIh) (IIh*) | phosphodiester | X = OH | Y = O |

(the phosphodiesters IIh or IIh* being especially preferred), especially 2'-deoxy derivatives (Q=H) or 2'-(2-methoxy)ethoxy (2'-O—CH₂CH₂OCH₃) derivatives, the remaining internucleosidic bonds in the respective oligonucleotide derivative being of the phosphorothioate type; for synthesis see European Application EP 0 626 387 and International Application WO 92/20823; or as oligonucleotide derivative which comprises at least one of the following dimeric units (bivalent radicals) of the formulae given hereinafter, wherein each B is, independently of the other, a base radical as defined above, preferably of a base selected from thymine, uracil, 5-propynyluracil, cytosine, 5-methylcytosine, 5-propynylcytosine, adenine, 2-aminoadenine and guanine; any Q is, indepently of the other, H, OCH₃, F or O(CH₂CH₂O)ᵥCH₃ wherein v is from 0 to 12, especially 1; and the other moieties have the meanings given behind the respective formula:

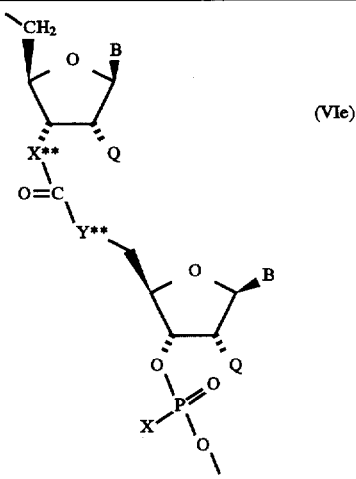

| Radical of formula | type | X | Y |
|---|---|---|---|
| (VIe), (VIe*) | amide | CH₂ | N(A) | wherein A is H, methyl or phenyl, preferably H; the remaining internucleosidic bonds in the respective oligonucleotide derivative being of the phosphorothioate type; for synthesis see International Application WO 95/20597and International Application WO 92/20823; or (alternatively or in addition) as oligonucleotide derivative which is present in the form of a chimeric oligonucleotide which shows, on the one hand, M regions of between 3 and 20 (preferably 5 to 15) modified building blocks (either with phosphodiester or with phosphorothioate backbone), especially 2'-(2-methoxy)ethoxy (more preferred) or 2'-F modified building blocks, which are in succeeding order; and, on the other hand, U regions of 4 to 20 2'-deoxy building blocks with phosphorothioate structure that are otherwise unmodified; preferably, the M and U regions being in one of the following arrangements:

5'-M-U-M-3'
5'-M-U-3' or
5'-U-M-3';

or especially oligonucleotide derivatives, preferably oligo-2'-deoxynucleotide derivatives, where all internucleosidic bridges as of the phosphorothioate type and that have no sugar or base modification; and b) at least one other chemotherapeutic agent selected from cross-linking chemotherapeutics, preferably bis-alkylating agents, especially nitrogen mustards, such as mechlorethamine (Mustargen); alkyl sulfonates such as busulfan (Myeleran); cyclophosphamide; melphalan (Alkeran); chlorambucil (Leukeran); cis-platinum(II)-diaminedichloride (platinol or cisplatin) or carboplatin (Paraplatin); or compounds that form cross-links via ionic bonds, such as ethyleneimine derivatives, e.g. triethylenethiophosphoramid (thio-tepa) (forms ionic cross-links); chemotherapeutic agents selected from cross-linking (bis-alkylating) antitumor antibiotics, such as mitomycin C (Mitomycin, Mutamycin); or vinca alkaloids, such as vinblastine (Velban), vincristine (Oncovin) or vindesine; most preferably a standard chemotherapeutic agent selected from the group comprising cisplatin, mitomycine and vinblastine;

where any component a) and/or b) can also be present in the form of a pharmaceutically acceptable salt, if at least one salt-forming group is present.

Still more preferred is a combination where in any of the embodiments of the invention defined above component b) is selected from the mentioned other chemotherapeutic agents except for adriamycin (doxorubicin), cyclophosphamide or an oligonucleotide or oligonucleotide derivative targeted at raf, especially human c-raf.

Even more preferred is a combination of a) at least one oligonucleotide derivative (ODN) targeted to nucleic acids encoding human PKC-α and that corresponds to the following sequence:

5'-GTT CTC GCT GGT GAG TTT CA-3'    SEQ. ID NO:1, (or also a version thereof which is terminally shortened on one or both ends, e.g. with 15 to 19 building blocks, most especially the derivative as such)

which is preferably present as an oligonucleotide derivative which (in its nucleotide/nucleotide derivative sequence) comprises at least one of the following units of the formulae given hereinafter, wherein B is a base radical as defined above, preferably of a base selected from thymine, uracil, 5-propynyluracil, cytosine, 5-methylcytosine, 5-propynylcytosine, adenine, 2-aminoadenine and guanine; Q is H, OCH₃, F, O(CH₂CH₂O)$_v$CH₃ wherein v is from 0 to 12, especially 1 or 3, CH₂CH(CH₃)OCH₃ or CH₂CH(OH)CH₂OH, or less preferably SH; and the other moieties have the meanings given behind the respective formula:

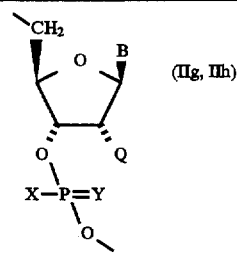

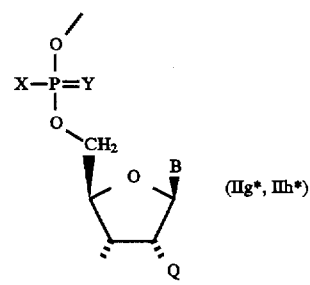

| Radical of formula | type | | |
|---|---|---|---|
| (IIg), (IIg*) | phosphorothioate | X = SH | Y = O or S |
| (IIh), (IIh*) | phosphodiester | X = OH | Y = O |

(the phosphodiesters IIh or IIh* being especially preferred), especially 2'-deoxy derivatives (Q=H) or 2'-(2-methoxy)ethoxy (2'-O—CH₂CH₂OCH₃) derivatives, the remaining internucleosidic bonds in the respective oligonucleotide derivative being of the phosphorothioate type; for synthesis see European Application EP 0 626 387 and International Application WO 92/20823; or as oligonucleotide derivative which comprises at least one of the following dimeric units (bivalent radicals) of the formulae given hereinafter, wherein each B is, independently of the other, a base radical as defined above, preferably of a base selected from thymine, uracil, 5-propynyluracil, cytosine, 5-methylcytosine, 5-propynylcytosine, adenine, 2-aminoadenine and guanine; any Q is, indepently of the other, H, $OCH_3$, F or $O(CH_2CH_2O)_vCH_3$ wherein v is from 0 to 12, especially 1; and the other moieties have the meanings given behind the respective formula:

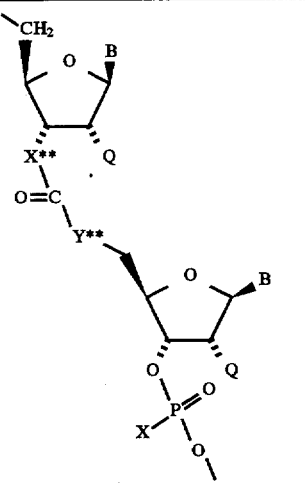

(VIe)

| Radical of formula | type | X** | Y** |
|---|---|---|---|
| (VIe), (VIe*) | amide | $CH_2$ | N(A) | wherein A is H, methyl or phenyl, preferably H; the remaining internucleosidic bonds in the respective oligonucleotide derivative being of the phosphorothioate type; for synthesis see International Application WO 95/20597 and International Application WO 92/20823; or (alternatively or in addition) as oligonucleotide derivative which is present in the form of a chimeric oligonucleotide which shows, on the one hand, M regions of between 3 and 20 (preferably 5 to 15) modified building blocks (either with phosphodiester or with phosphorothioate backbone), especially 2'-(2-methoxy) ethoxy (more preferred) or 2'-F modified building blocks, which are in succeeding order; and, on the other hand, U regions of 4 to 20 2'-deoxy building blocks with phosphorothioate structure that are otherwise unmodified; preferably, the M and U regions being in one of the following arrangements:

5'-M-U-M-3'
5'-M-U-3' or
5'-U-M-3';

especially oligonucleotide derivatives, preferably oligo-2'-deoxynucleotide derivatives, where all internucleosidic bridges as of the phosphorothioate type and that have no sugar or base modification; and b) at least one other chemotherapeutic agent selected from the group comprising cisplatin, mitomycine and vinblastine, especially one of cisplatin and mitomycine;

where any component a) and/or b) can also be present in the form of a pharmaceutically acceptable salt, if at least one salt-forming group is present.

Much more preferred is a combination of a) one of the oligonucleotide derivatives mentioned in any previous definition and b) at least one, preferably one or two, of the chemotherapeutic agents mentioned in any of the preceding definitions.

Still more preference is given to a combination according to any of the preceding embodiments of the invention where the disease to be treated is selected from prostate carcinoma, lung carcinoma, especially large lung cell carcinoma, and breast cancer.

Very high preference is given to a combination wherein
a) an oligonucleotide derivative that corresponds to the following sequence:

5'-GTT CTC GCT GGT GAG TTT CA-3'    SEQ. ID NO:1, (or also a version thereof which is terminally shortened on one or both ends, e.g. with 15 to 19 building blocks, most especially the derivative as such)
which is present in the form of a phosphorothioate oligo-2'-deoxynucleotide analogue, and b) any one of the following other chemotherapeutic agents for the treament of the respective proliferative disease:
cisplatin for human prostate carcinomas;
mitomycin for large cell lung carcinomas; and
vinblastine for breast cancer;

are in combination; where any component a) and b) can also be present in the form of a pharmaceutically acceptable salt, if at least one salt-forming group is present.

Highest preference is given to the combinations provided in the examples, more especially the synergistic combinations given there, most specific the combinations where component b) is not selected from adriamycin, an ODN targeted at raf kinase and cyclophosphamide alone.

Explicitly preferred is a synergistic combination and/or a combination leading to regression of proliferating cells up to and including complete cure, especially a synergistic combination, according to any of the embodiments of the invention defined above or given in the examples.

Explicitly preferred among all combinations is one wherein component a) is an oligonucleotide derivative which is present in the form of a chimeric oligonucleotide which shows, on the one hand, M regions of between 3 and 20 (preferably 5 to 15) modified building blocks (either with phosphodiester or with phosphorothioate backbone), especially 2'-(2-methoxy)ethoxy modified building blocks, which are in succeeding order; and, on the other hand, U regions of 4 to 20 2'-deoxy building blocks with phosphorothioate structure that are otherwise unmodified; preferably, the M and U regions being in one of the following arrangements:

5'-M-U-M-3'
5'-M-U-3' or
5'-U-M-3'

The oligonucleotides and their derivatives in accordance with this invention may be conveniently and routinely made in analogy to or through methods and using starting materials well-known in the art (for reviews, see, inter alia, Milligan et al., J. Med. Chem. 36(14), 1923–37 (1993) and Uhlmann et al., Chemical Rev. 90(4), 543–84 (1990); see also International Application WO 92/20823 published 11. Nov. 1992), for example by the well-known technique of solid phase synthesis. Equipment for such synthesis is sold by several vendors (e.g., Applied Biosystems Inc., Foster City, Calif., USA). Any other means for such synthesis may also be employed; the actual synthesis of the oligonucleotides is well within the talents of the routineer. It is also well known to use similar techniques to prepare other oligonucleotide derivatives such as the phosphorothioates and nucleoside modified derivatives.

Most preferably, phosphorothioate analogues of the invention can be made by methods known in the art, preferably by reacting a starting material which contains a 5' terminal fragment of the formula XIII,

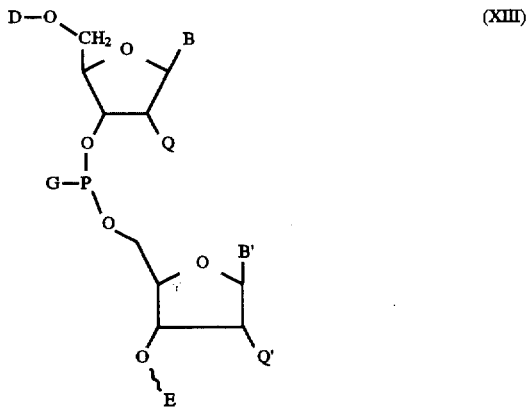

(or a tautomer thereof) wherein D is a hydroxy protecting group, B and B' independently represent bases as defined above for B in any one of formulae I to X, Q and Q' independently represent H, OH, SH, SCH3, F, $N_3$, CN, OCN, $OCH_3$, $O(CH_2)_z NH_2$ or $O(CH_2)_z CH_3$ where z is from 1 to about 10, $O(CH_2CH_2O)_v CH_3$ wherein v is from 0 to 12, especially 1 or 3, $CH_2CH(CH_3)OCH_3$ or $CH_2CH(OH)CH_2OH$, or in a broader sense another substituent having similar properties, for example selected from Cl, Br, $CF_3$, $ONO_2$, $NO_2$, $NH_2$ and O—, S— or NH-lower alkyl, most especially Q being hydroxy or preferably —O—$CH_2CH_2OCH_3$ or (most preferably) hydrogen; and the other moieties have the meanings given behind the respective formula; G is hydrogen, lower alkoxy or 2-cyanoethoxy and E is a hydroxy protecting group, a carrier or a 3' free or carrier-bonded mono- or oligonucleotide analogue wherein in place of any phosphodiester group {O—[P(=O)(—OH)]—O} a phosphorothioate analogue {O—[P(=S)(—OH)]—O}/{O—[P(—SH)(=O)] or a group of the formula {O—[(P=O)—H]—O}/{O—(P—OH)—O} is present, with a sulfurylating reagent with simultaneous oxidation of any trivalent phosphorus being present, where necessary further functional groups being in protected form, and, where necessary, removing any protecting groups and/or carriers, and, if desired, separating any resulting mixtures of isomers into the individual isomers, and/or transforming a resulting free phosphorothioate oligonucleotide into a salt, and/or transforming a resulting salt into the free form or into a different salt.

In detail, the synthesis is preferably carried out as follows:

Any functional groups being present can be in unprotected or protected form, the protecting groups being selected from those mentioned above for OH or amino/imino groups (SH protecting groups can be selected from those given above for hydroxy groups). A characteristic of these protecting groups is that they are not present in the final products. Protecting groups can be removed by standard methods known in the art, such as those mentioned in the references given above.

D is preferably the dimethoxytrityl group; this group can be removed preferably by acid hydrolysis, for example with mild acids such as formic acid, acetic acid, dichloroacetic acid or furthermore trifluoroacetic acid, in water or organic solvents such as halogenated solvents, for example dichloromethane, cyclic ethers, for example tetrahydrofurane, or lower-alkylcyanides, for example acetonitrile, or mixtures thereof.

It is most preferred that the terminal hydroxy protecting group D in the resulting phosphorothioate oligonucleotide is removed in a step separate from and after the removal of further protecting groups, such as acetyl, benzoyl, phenoxyacetyl, 4-tert-butylphenoxyacetyl, N,N-dimethylformamidinyl, N-methylpyrrolidin-2-yliden, succinyl, 2-cyanoethyl and similar protecting groups that can be removed in a first deprotection step by basic hydrolysis, preferably in the presence of a nitrogen base, such as ethanolamine in an alcohol, such as ethanol, or preferably in the presence of ammonium hydroxide in an aqueous solvent, such as water, at temperatures ranging preferably from about 10° to about 80° C., and then purify the resulting OH-protected oligonucleotide derivative by chromatography on lipophilic adsorbents, such as reverse phase HPLC material, and then, in the purified oligonucleotide derivative, finally removing the OH protecting group, preferably the dimethoxy trityl group, by acid hydrolysis as described above.

B and B' preferably each represent a radical derived from one of the bases adenine, guanine, thymine, cytosine or 5-methylcytosine.

G is preferably 2-cyanoethoxy, the 3' free or carrier-bonded mono- or oligonucleotide analogue then being one wherein, in place of any phosphodiester group {O—[P(=O)(—OH)]—O}, a phosphorothioate analogue {O—[P(=S)(—OH)]—O}/{O—[P(—SH)(=O)] is present.

If G is OH, the 3' free or carrier-bonded mono- or oligonucleotide analogue can be one wherein either in place of any phosphodiester group {O—[P(=O)(—OH)]—O} a phosphorothioate group {O—[P(=S)(—OH)]—O}/{O—[P(—SH)(=O)—two tautomeric forms] is present or one ore more groups of the formula {O—[(P=O)—H]—O}/{O—(P—OH)—O} (two tautomeric forms) are present instead of one or more, maximally all, phosphorothioate bonds. In the latter case, in the process according to the invention all phosphorus atoms in the respective oligonucleotide can be thiolated simultaneously.

E is preferably a 3' free or carrier-bonded mono- or oligonucleotide analogue wherein in place of any phosphodiester group {O—[P(=O)(—OH)]—O} a phosphorothioate analogue {O—[P(=S)(—OH)]—O}/{O—[P(—SH)(=O)] or a group of the formula {O—[(P=O)—H]—O}/{O—(P—OH)—} (two tautomeric forms) is present.

Where possible, any starting material can also be present in the form of a salt.

A sulfurylating reagent which is capable of reaction with simultaneous oxidation of any trivalent phosphorus being present, is, for example, selected from the group comprising $S_8$ in an organic solvent in the presence of a nitrogen base, such as $S_8$ in pyridine/triethylamine or $S_8$ in 2,6-lutidine; sulfur in $CS_2$ in the presence of a nitrogen base, such as triethylamine or pyridine; 3H-1,2-benzodithiol-3-one-1,1-dioxide in acetonitrile; and most preferably diisopropoxy-thiophosphoric acid disulfide of the formula XIV

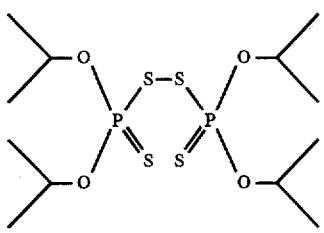

(XIV)

in an organic solvent, such as acetonitrile, in the presence of a tertiary nitrogen base, such as pyridine. The preferred temperatures are in the range from 10° to 80° C., most preferably around room temperature.

The starting material with a fragment according to formula XIII (which makes the respective oligonucleotide complete with respect to the number of nucleotide units) can be synthesized according to methods known in the art, preferably by a combination of standard cyanoethyl phosphoramidite chemistry and simultaneous sulfurylation plus oxidation plus a further step according to standard cyanoethyl amidite chemistry to yield the corresponding triester starting materials (G being lower alkyl or 2-cyanoethyl in formula XIII) or (especially if several phosphodiester groups are present in the starting material of formula XIII due to an appropriate group E corresponding to an oligonucleotide analogue wherein in place of any phosphodiester group a group of the formula {O—[(P=O)—H]—O}/{O—(P—OH)—O} is present) H-phosphonate chemistry (see Uhlmann et al., Chemical Reviews 90(4), 543–84 (1990) for review and further references).

To synthesize oligonucleotide derivatives with one or more building blocks of any one of formulae I and I* to X and X* wherein Q is O(CH$_2$CH$_2$O)$_v$CH$_3$ wherein v has the meanings defined above, and the other moieties are as defined, the respective starting material (either a building block or a complete oligonucleotide or its derivative) wherein at least one Q is hydroxy can, for example, be reacted in an inert solvent with a compound of formula XV,

X—(CH$_2$—CH$_2$—O)$_v$—CH$_3$  (XV)

wherein X is a leaving group and v is as defined above, functional groups being present in the starting materials being protected by protecting groups as defined above which can be removed at appropriate stages.

A leaving group X may, for example, be halogen, such as Cl, Br or I, arylsulfonyl, such as 4-toluolsulfonyl, or lower alkane sulfonyl, such as mesyl-sulfonyl.

The reaction is carried out preferably in the presence of a strong base, such as an alkali metal hydride, for example NaHl, in an inert solvent, such as an ether, for example a cyclic ether, such as tetrahydrofurane, at temperatures ranging from 30° C. to the boiling point of the reaction mixture, preferably under reflux conditions.

For the synthesis of oligonucleotide derivatives which (in their nucleotide/nucleotide derivative sequence) comprise at least one of the units (bivalent radicals) of the formulae IIg and IIh or IIg* and IIh* given hereinbefore, wherein B is a base radical as defined above, preferably of a base selected from thymine, uracil, 5-propynyluracil, cytosine, 5-methylcytosine, 5-propynylcytosine, adenine, 2-aminoadenine or guanine; Q is H, O(CH$_2$CH$_2$O)$_v$CH$_3$ wherein v is from 0 to 12, especially 1 or 3, CH$_2$CH(CH$_3$)OCH$_3$ or CH$_2$CH(OH)CH$_2$OH; and the other moieties have the meanings given behind the respective formula, synthesis is possible according to or in analogy to known procedures (see European Application EP 0 626 387 and International Application WO 92/20823); for oligonucleotide derivatives which comprise at least one of the units (bivalent radicals) of the formulae VIe and VIe* given hereinbefore, wherein B is a base radical as defined above, preferably of a base selected from thymine, uracil, 5-propynyluracil, cytosine, 5-methylcytosine, 5-propynylcytosine, adenine, 2-aminoadenine or guanine; Q is OCH$_3$ or O(CH$_2$CH$_2$O)$_v$CH$_3$ wherein v is from 0 to 12, especially 1; and the other moieties have the meanings given behind the respective formula, synthesis is also possible in accordance with or in analogy to known procedures (see International Application WO 95/20597 and International Application WO 92/20823).

The separating of any resulting mixtures of isomers into the individual isomers can be done according to methods well-known in the art, for example using chromatographic procedures in order to separate diastereomers. Separation at the stage of a starting material or small intermediates is preferred due to possible difficulties in the separation of larger oligonucleotides/oligonucleotide derivatives. Separation of isomers is not mandatory to achieve the desired biological activity.

The transformation of resulting free compounds into their salts can be achieved according to standard methods, salts of cationic groups for example being available by treatment with appropriate acids or anion exchangers, and salts of anionic groups being available by treatment with an appropriate base or cation exchanger; or preferably by dialysis of the respective compound against a solution of the desired cation.

Salts can be transformed into the free compounds according to standard procedures, metal or ammonium salts for example by treatment with an appropriate acid or an acidic ion exchanger, acid addition salts by treatment with an appropriate base or basic ion exchanger.

The transfer of salts into different salts is possible in analogy to the transformation of a free compounds into a salt, as mentioned above.

The above-mentioned reactions can be carried out under reaction conditions that are known per se, in the absence or customarily in the presence of solvents or diluents, preferably those solvents and diluents that are inert towards the reagents used and are solvents therefore, in the absence or presence of catalysts, condensation agents or neutralising agents, depending on the nature of the reaction and/or the reactants at reduced, normal or elevated temperature, e.g. in a temperature range of from approximately −80° C. to approximately 250° C., preferably from approximately −20° C. to approximately 150° C., for example from room temperature to the reflux temperature, under atmospheric pressure or in a closed vessel, if desired under pressure, for example at the pressure produced in the reaction mixture under the reaction conditions in a closed tube, and/or in an inert atmosphere, e.g. under an argon or nitrogen atmosphere. The reaction conditions specifically mentioned in PCT application WO 95/32987 are preferred.

Solvents and diluents are, for example, water, alcohols, for example lower alkanols, such as methanol, ethanol or propanol, diols, such as ethylene glycol, triols, such as glycerol, or aryl alcohols, such as phenol, acid amides, for example carboxylic acid amides, such as dimethylformamide, dimethylacetamide or 1,3-dimethyl-3,4,5,6-tetrahydro-2(1H)-pyrimidinone (DMPU), or amides of inorganic acids, such as hexamethylphosphoric acid triamide, ethers, for example cyclic ethers, such as tetrahydrofuran or dioxane, or acyclic ethers, such as diethyl ether or ethylene glycol dimethyl ether, halogenated hydrocarbons, such as halo-lower alkanes, for example methylene chloride or chloroform, ketones, such as acetone, nitriles, such as acetonitrile, acid anhydrides, such as acetic anhydride, esters, such as ethyl acetate, bisalkane sulfines, such as dimethyl sulfoxide, nitrogen heterocycles, such as pyridine, hydrocarbons, for example lower alkanes, such as heptane, or aromatic compounds, such as benzene or toluene, or mixtures of those solvents, it being possible to select the particular solvents that are suitable for each of the above-mentioned reactions.

In view of the close relationship between the oligonucleotides or oligonucleotide derivatives that have the properties according to the invention and the precursors thereof in free form and in the form of salts and/or tautomers, hereinbefore and hereinafter any reference to the free compounds and starting materials or the salts and/or tautomers thereof should be understood as including the corresponding salts or free compounds and/or tautomers, respectively, as appropriate and expedient, provided that the compounds contain one or more salt-forming groups, e.g. basic groups, such as amino or imino groups, and/or acidic groups, such as carboxy, phosphoric acid radicals or sulfo ($SO_3H$), and/or tautomerisable groups. In connection with starting materials, intermediates or final products, any reference made hereinbefore and hereinafter to a substituent, a compound, a tautomer or a salt, or to substituents, compounds, tautomers or salts, is to be understood, irrespective of whether the singular or the plural is used, as meaning "one or more" as appropriate and expedient. Starting materials may also be used in protected form, where necessary, appropriate and expedient, it being possible for the protecting groups to be removed at suitable times. Protecting groups, their introduction and their removal are especially as defined above.

The compounds, including their salts, may also be obtained in the form of hydrates, or their crystals may include, for example, the solvent used for crystallisation.

In the process of the present invention the starting materials used are preferably those that result in the compounds described at the beginning as being preferred.

The description relates also to those forms of the process in which a compound obtainable as intermediate at any stage of the process is used as starting material and the remaining process steps are carried out, or in which a starting material is formed under the reaction conditions or is used in the form of a derivative, for example a salt, thereof.

The sequence and reaction conditions of all the described reactions are preferably to be so selected as considered appropriate and expedient to the person skilled in the art.

Pharmaceutical Compositions and Processes

The pharmaceutical compositions that can find use in a combination according to the invention are comprising either one or more of the components a) (an oligonucleotide or an oligonucleotide derivative) and b) (other chemotherapeutic agent) with the properties according to the invention as active ingredient, which can be used alone (e.g. as fixed combination) or as kit of parts. Especially preferred are compositions for enteral, especially oral, or parenteral administration. The compositions comprise the active ingredient or combinations thereof as such or, preferably, together with a pharmaceutically acceptable carrier. The dose of any active ingredient depends on the disease to be treated, and on the species, age, weight and individual condition, as well as the method of administration.

Preferred is a pharmaceutical composition or combination that is suitable for administration to a warm-blooded animal, especially man, suffering from a proliferative disease selected from hyperproliferative conditions such as cancers, tumors, hyperplasias, fibrosis, angiogenesis, psoriasis, atherosclerosis and smooth muscle cell proliferation in the blood vessels, such as stenosis or restenosis following angioplasty. Most preferably, the disease is one selected from cancer types which have been very difficult to treat or even practically unaffected by therapy with standard chemotherapeutics, such as small cell lung carcinoma, large cell lung carcinoma, melanoma, prostate carcinoma or further also lymphoma. Most preferably, any of the aforementioned proliferative diseases that can be treated by inhibition of human PKC-α activity is meant, especially selected from prostate carcinoma, lung carcinoma, especially large lung cell carcinoma, and breast cancer.

The pharmaceutical compositions comprise from approximately 0.0001% to approximately 95% active ingredient, dosage forms that are in single dose form preferably comprising from approximately 0.001% to approximately 20% active ingredient, and dosage forms that are not in single dose form preferably comprising from approximately 0.001% to approximately 10% active ingredient. Unit dose forms, such as dragées, tablets, ampoules or capsules, comprise from approximately 0.0005 mg to approximately 0.5 g of the active ingredient, preferably from 0.005 mg to approximately 40 mg.

The pharmaceutical compositions are prepared in a manner known per se, for example by means of conventional mixing, granulating, confectioning, dissolving or lyophilising processes. For example pharmaceutical compositions for oral administration can be obtained by combining the active ingredient with one or more solid or liquid carriers, where necessary granulating a resulting mixture and processing the mixture or the granules, if desired or appropriate with the addition of further excipients, to form tablets or dragée cores or solutions, respectively.

Suitable carriers are especially fillers, such as sugars, e.g. lactose, saccharose, mannitol or sorbitol, cellulose preparations and/or calcium phosphates, e.g. tricalcium phosphate or calcium hydrogen phosphate, and binders, such as starches, e.g. corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, and also carboxymethyl starch, crosslinked polyvinylpyrrolidone or alginic acid or a salt thereof, such as sodium alginate. Additional excipients are especially flow conditioners and lubricants, e.g. silicic acid, talc, stearic acid or salts thereof, such as magnesium or calcium stearate, and/or polyethylene glycol, or derivatives thereof.

Dragée cores may be provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or dragée coatings, e.g. for identification purposes or to indicate different doses of active ingredient.

Orally administrable pharmaceutical compositions are also dry-filled capsules consisting of gelatin, and also soft sealed capsules consisting of gelatin and a plasticiser, such as glycerol or sorbitol. The dry-filled capsules may contain the active ingredient in the form of granules, for example in admixture with fillers, such as corn starch, binders and/or glidants, such as talcum or magnesium stearate, and, where appropriate, stabilisers. In soft capsules, the active ingredient is preferably dissolved or suspended in suitable liquid excipients, e.g. fatty oils, ®Lauroglycol (Gattefossé S. A., Saint Priest, France), ®Gelucire (Gattefossé S. A., Saint Priest, France) or sesame oil, paraffin oil or liquid polyethylene glycols, such as PEG 300 or 400 (Fluka, Switzerland), or polypropylene glykols, to each of which stabilisers or detergents may also be added, on in water comprising further soluble carriers as mentioned above, such as methylcellulose or mannitol.

Other oral forms of administration are, for example, solutions or syrups prepared in customary manner that comprise the active ingredient e.g. in suspended form and in a concentration of approximately from 0.001% to 20%, preferably approximately 0.001% to about 2%, or in a similar concentration that provides a suitable single dose when administered, for example, in measures of 0.5 to 10 ml. Also suitable, for example, are powdered or liquid concentrates for preparing shakes, e.g. in milk. Such concentrates can also be packed in single-dose quantities.

Transdermal Delivery Systems are possible, especially with neutral active ingredients. Suitable formulations comprise, for example, about 0.0001% to about 2% by weight of active ingredient. In a preferred aspect, there are provided formulations which comprise about 2% to 99.9999% (or the balance to 100%) of a short chain aliphatic alcohol. Suitable alcohols include ethanol, isopropanol, propylene glycol and glycerol. In a more preferred aspect, these formulations may additionally comprise a flux enhancer. Suitable flux enhancers include, for example, decylmethylsulfoxide, dimethylsufoxide as well as cyclic ketones, lactones, anhydrides and esters. Some of these flux enhancers also increase retention of the active ingredient and thus act to increase the concentration of it in the skin itself. For formulations for direct (local) treatment, such as topical application to the skin, it is preferred to use a flux enhancer which not only maximizes transdermal flux, but increases retention of the active ingredient in the skin. Certain cyclic ketone and lactone enhancers have been reported to increase local retention as well and, thus, comprise a preferred class of enhancers for topical administration of the active ingredient. In formulations for systemic treatment, it is preferable to use a flux enhancer which maximizes flux with a minimal local retention of the active ingredient.

Suitable rectally administrable pharmaceutical compositions are e.g. suppositories that consist of a combination of the active ingredient with a suppository base. Suitable suppository bases are e.g. natural or synthetic triglycerides, paraffin hydrocarbons, polyethylene glycols or higher alkanols.

For parenteral administration there are suitable, especially, aqueous solutions of an active ingredient in water-soluble form, e.g. in the form of a water-soluble salt, in the presence or absence of salts, such as sodium chloride, and/or sugar alcohols, such as mannitol, or aqueous injection suspensions that comprise viscosity-increasing substances, e.g. sodium carboxymethylcellulose, sorbitol and/or dextran, and, where appropriate, stabilisers. The active ingredient, where appropriate together with excipients, may also be in the form of a lyophilisate and may be made into a solution prior to parenteral administration by the addition of suitable solvents.

Solutions as used e.g. for parenteral administration may also be used as infusion solutions.

Preferred formulations comprising any component b) (other chemotherapeutic agent) are those that are customary for the respective clinical use of any (especially standard) chemotherapeutic agent which are known in the art.

Preferred formulations for component a) are those mentioned in the examples.

The invention relates also to a method of treating the above-mentioned pathological conditions. For this purpose, in the combinations as hereinbefore described any active ingredient, or a pharmaceutically acceptable salt thereof, may be administered prophylactically or therapeutically, preferably in an amount that is effective against the mentioned diseases, to a warm-blooded animal, e.g. man, requiring such treatment, preferably in the form of a pharmaceutical composition. The dose of any active ingredient depends on the species of the warm-blooded animal to be treated, its body weight, its age and individual status, individual pharmacokinetic circumstances, the disease to be treated and the application route. Preferably, for a body weight of approximately 70 kg a daily dose of from 0.001 mg to 1000 mg, e.g. from approximately 0.01 mg to approximately 100 mg, preferably from approximately 0.05 mg to approximately 50 mg, of any active ingredient is administered.

The following examples illustrate the present invention without being intended to limit the scope thereof:

EXAMPLES

(A) Chemotherapeutic Drugs

Adriamycin is purchased from Farmitalia Carlo Erba (Italy). Estracyt is purchased from Kabi Pharmacia (Uppsala, Sweden). Cisplatin is from Bristol Meyers Squibb (USA). 5-Fluorouracil is from Hoffmann La Roche (Switzerland). Mitomycin is from Kyowa Hakko (Japan). Ifosfamide is purchased from Asta (Germany). Tamoxifen is from Farmos (Finnland). Vinblastine is from Lilly (Germany). The drugs are dissolved in the solutes given below and applied either p.o. (tamoxifen) or i.v. (adriamycin, ifosfamide, estracyt, cis-platin, 5-fluorouracil, mitomycin, vinblastine) according to the schedules indicated in the tables in the examples.

In combination studies the chemotherapeutic agents are applied as follows (if not indicated otherwise in the tables):

For i.v. application, the concentrations of the solutions are chosen such that the amount of active ingredient mentioned below is applied in 10 ml/kg of the indicated solution. For p.o. application, the concentrations of the solutions are chosen such that the amount of active ingredient mentioned below is applied in 25 ml/kg of the indicated solution.

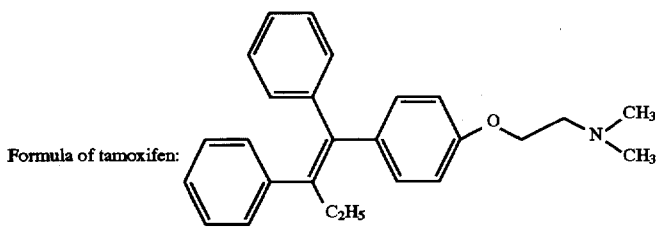

Formula of tamoxifen:

-Adriamycin: 9mg/kg i.v., once weekly.

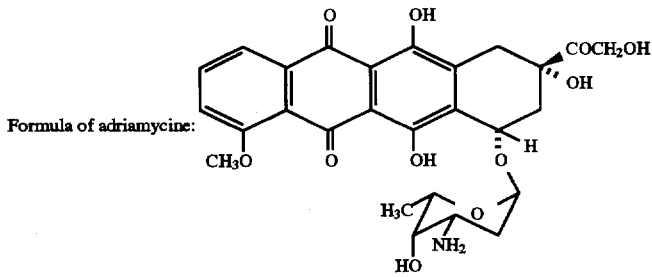

Formula of adriamycine:

-Isosfamide: 150 mg/kg i.v., once weekly.

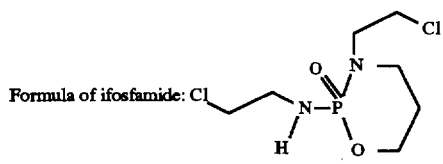

Formula of ifosfamide:

-Estracyt: 50 mg/kg i.v., daily in 5% mannitol.

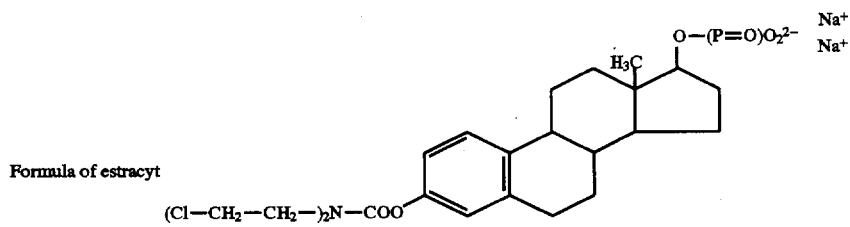

Formula of estracyt

-Cisplatin: 10 or 11 mg/kg i.v., once weekly in pharmacopoe (10 or 11 mg of USP cisplatin RS in 10 ml 0.9% NaCl/1% D-mannitol).

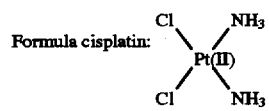

Formula cisplatin:

-5-Fluorouracil: 75 mg/kg i.v., once weekly.

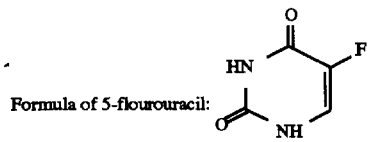

Formula of 5-flourouracil:

-Mitomycin: 3.5 mg/kg i.v., once weekly.

Formula of mitomycin:

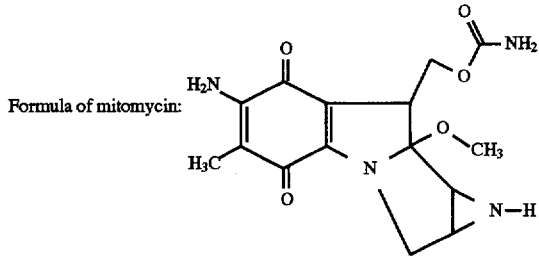

-1.5 mg/kg i.v., once weekly

Formula of vinblastine:

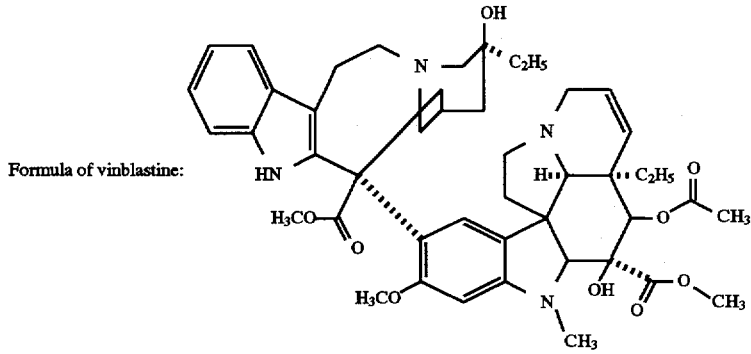

(B) ODNs

Phosphorothioate oligodeoxynucleotides (ODNs) are synthesized on a 0.5 mmole scale using a Milligen model 8800 DNA synthesizer (Bedford, Mass.) using modified phosphoramidite chemistries with β-cyanoethoxyphosphoramidites. Crude product of approximately 70% purity is further purified by orthogonal columns chromatography using a Millipore HC18-HA column followed by anion exchange chromatography using a Millipore Q-15 strong anion exchanger. The purified material is precipitated from ethanol, redissolved and further desalted by ultrafiltration. The samples are depyrogenated by ultrafiltration with endotoxin levels reduced to below detectable levels using a standard endotoxin assay. 5'-GTT CTC GCT GGT GAG TTT TT-3'; SEQ ID NO: 1 is a 20-mer phosphorothioate ODN targeting the 3'-untranslated region of PKC-α mRNA which is used in the following examples, where it is named SEQ-ID NO: 1-ODN.

(C) Antitumor Activity in Vivo

Female or male Balb/c nude mice are obtained from Bomholtgaard, Kopenhagen, Denmark or Ciba animal breeding facility, Sissein, Switzerland. For the testing of in vivo antitumor activity, SEQ-ID NO: 1-ODN is dissolved in sterile saline (0.6 mg/ml) and is tested in a dose-range of 0.006 to 6 mg/kg once daily by the intravenous route of application. If not indicated otherwise, data with standard error of the mean are given for 6 mice per time point, respectively. Placebo treated controls receive carrier as indicated in examples. The following human tumor cells are used for the experiments:

Estrogen receptor-positive breast cancer: MCF-7.
Colon cancers: Colo 205, WiDr.
Small cell lung carcinomas: NCl-H69.
Large cell lung carcinoma: NCl-H460.
Squamous cell carcinoma: NCl-H520.
Melanoma: SK-mel 1.

Prostate carcinomas: PC3, DU 145.

All the cell lines used are obtained from the American Type Culture Collection (ATCC) and are cultured in the suggested media and additives (ATCC culture conditions):

(i) MCF-7:ATCC HTB 22. These cells were taken from the pleural effusion of a 69-year old female Caucasian (see H. D. Soule et al., J. Natl. Cancer Inst. 51, 1409–16 (1973)). Medium for propagation: Medium: Eagle's MEM with non-essential amino acids, sodium pyruvate, 20 ug insulin/ml, 10% fetal calf serum.

(ii) Colo 205: ATCC CCL 222. This cell line was isolated from ascitic fluid of a 70-year-old Caucasian male with carcinoma of the colon (see Cancer Res. 38, 1345–55 (1978)). Medium for propagation: RPMI 1640, 90%; heat-inactivated fetal bovine serum, 10%.

(iii) WiDr:ATCC CCL 218. The cell line was initiated through explant culture of tissue from a primary adenocarcinoma of the rectosigmoid colon from a 78-year-old female (see In Vitro 15, 401–8 (1979)). Medium for propagation: Eagle's Minimal Essential Medium with non-essential amino acids and Earle's BSS, 90%; fetal bovine serum, 10%.

(iv) NCl-H69: ATCC HTB 119. The cell line was derived from the pleural fluid of a 55-year-old Caucasian male with small cell carcinoma of the lung (see Cancer Res. 40, 3502–7 (1980)). Medium for propagation: RPMI 1640, 90%; fetal bovine serum, 10%.

(v) NCl-H460: ATCC HTB 177. This cell line was designed from the pleural fluid of a male with large lung cell carcinoma in 1982 (see A. F Gazdar et al., Science 246, 491–494 (1989)) Medium for propagation: RPMI 1640, 10% fetal calf serum.

(vi) NCl-H520: ATCC HTB 182. This cell line was established in serum-free medium in 1982 from a lung mass taken from a male with squameous cell carcinoma of the lung (see Cancer Res. 46, 798–806 (1986)). Medium for propagation: RPMI 1640, 90%; fetal bovine serum, 10%.

(vii) SK-mel 1: ATCC HTB 67. The cell line was isolated using cells obtained from the thoracic duct of a patient with widespread and rapidly progressing malignant melanoma (J. Natl. Cancer Inst. (Bethesda) 41, 827–31 (1968)). Medium for propagation: Eagle's Minimal Essential Medium with non-essential amino acids, sodium pyruvate (1 mM) and Earle's BSS, 90%; fetal bovine serum, 10%.

(viii) PC3: ATCC CRL 1435. The cell line was initiated from a grade IV prostatic adenocarcinoma from a 62-year-old male Caucasian (see Invest. Urol. 17, 16–23 (1979) and Cancer Res. 40, 524–34 (1980)). Medium for propagation: Ham's F12K medium, 93%; fetal bovine serum, 7%.

(ix) DU145: ATCC HTB 81. This cell line was isolated by K. R. Stone and associates fro a lesion in the brain of a patient with widespread metastatic carcinoma of the prostate and a 3-year history of lymphocytic leukemia (see D. D. Mickey et al. Cancer Res. 37, 4049–4058, (1977)). Medium for propagation: Eagle's MEM, 10% fetal calf serum.

Animals are kept under sterile conditions with free access to food and water. For all in vivo experiments, tumors are serially passaged by a minimum of three consecutive transplantations prior to start of treatment. Tumor fragments (approx. 25 mg) are implanted s.c. into the left flank of the animals with a 13-gauge trocar needle under Forene (Abbott, Switzerland) anesthesia. Treatments are started when the tumors reach a mean tumor volume of approximately 100 $mm^3$. Tumor growth is monitored twice weekly and 24 hours after the last treatment by measuring perpendicular diameters. Tumor volumes are calculated as described (Evans, B D, Mith, I E, Shorthouse, A J, Millar, J J. A comparison of the response of human cell carcinoma to vindesine and vincristine. Brit. J. Cancer 45, 466–468 (1982)). T/C % data are percent values of Tumor versus Control.

Treatment with the respective compounds or combinations was made according to the following time schedule in the Examples mentioned hereinafter:

Example Time Schedule for Administration

Ex. 1 placebo and SEQ-ID NO: 1-ODN: once daily for 22 consecutive days starting with day 7 after tumor transplantation; adriamycin: once weekly on days 7, 14 and 21; vinblastine: once weekly for 3 consecutive weeks (on days 7, 14 and 21); tamoxifen: three times weekly on days 7–9, 14–16 and 21–23, respectively.

Ex. 2 placebo: twice daily for 21 consecutive days, starting with day 12 after tumor transplantation; SEQ-ID NO: 1-ODN: once daily for 21 consecutive days, starting with day 12 after tumor transplantation; estracyt: once daily for 21 consecutive days, starting on day 12 after transplantation; cisplatin: once weekly on days 12 and 19 after transplantation.

Ex. 3 placebo: once daily for 14 consecutive days, starting with day 9 after tumor transplantation; SEQ ID NO: 1-ODN and estracyt: once daily for 14 consecutive days, starting with day 9 after tumor transplantation; cisplatin: once a week on days 9 and 16 after tumor transplantation.

Ex. 4 placebo and SEQ ID NO: 1-ODN: once daily for 17 consecutive days, starting from day 12 after transplantation; fluorouracil: once weekly on days 12, 19 and 26 after transplantation; adriamycin: once weekly on days 12, 19 and 26 after transplantation.

Ex. 5 placebo and SEQ-ID NO: 1-ODN: once daily for 25 consecutive days, starting on day 10 after transplantation; 5-fluorouracil: once weekly on days 10, 17, 24 and 28 after tumor transplantation; adriamycin: once weekly on days 10, 17 and 24 after transplantation.

Ex. 6 placebo: once weekly on day 4 and 11 after transplantation; SEQ-ID NO: 1-ODN: once daily for 14 consecutive days, starting on day 4 after transplantation; mitomycin: once weekly on days 4, 11 and 18 after tumor transplantation; ifosfamide and cisplatin: once weekly on days 4 and 11 after transplantation.

Ex. 7 placebo and SEQ-ID NO: 1-ODN: once daily for 11 consecutive days, starting on day 8 after transplantation; adriamycin, mitomycin and ifosfamide: once weekly on days 8 and 15 after transplantation Ex. 8 placebo: once weekly on days 11, 18 and 25 after transplantation; adriamycin and mitomycin: once weekly on day 11, 18 and 25 after tumor transplantation; SEQ-ID NO: 1-ODN: once daily starting on day 11 after transplantation (D) Results Example 1: Effect of SEQ-ID NO: 1-ODN in Combination with Tamoxifen, Adriamycine or Vinblastine on the Growth of s.c. Transplanted Human Breast Carcinoma MCF-7 in Female Balb/c Nude Mice:

| Treatment | Tumor volume in $mm^3$ (mean ± sem) on | | | | | | T/C % |
|---|---|---|---|---|---|---|---|
| | day 7 | day 14 | day 17 | day 20 | day 23 | day 29 | |
| Placebo treated controls (NaCl 0.9%, 10 ml/kg i.v.) | 132 ±12 | 298 ±49 | 484 ±96 | 628 ±110 | 776 ±117 | 1132 ±186 | 100 |
| SEQ-ID: NO-1-ODN alone (NaCl 0.9%, 10 ml/kg i.v.) | 129 ±14 | 166 ±20 | 227 ±35 | 293 ±64 | 348 ±73 | 430 ±93 | 30 |
| Adriamycine alone (NaCl 0.9%, 9 mg/kg i.v.) | 132 ±17 | 227 ±53 | 280 ±66 | 327 ±66 | 378 ±60 | 457 ±54 | 32 |
| SEQ-ID: NO-1-ODN + adriamycine (6 mg/kg i.v. and 9 mg/kg i.v.) | 135 ±14 | 118 ±11 | 126 ±42 | 137 ±52 | 159 ±55 | 194 ±67 | 6 |
| vinblastine alone (NaCl 0.9%, 1.5 mg/kg i.v.) | 135 ±14 | 103 ±14 | 79 ±12 | 72 ±8 | 70 ±7 | 87 ±16 | −36 |
| SEQ-ID: NO-1-ODN + vinblastine (6 mg/kg i.v. and 1.5 mg/kg i.v.) | 129 ±14 | 60 ±15 | 33 ±10 | 11 ±6 | 3 ±4 | 0 ±0 | * |
| Tamoxifen alone (methyl-cell. 0.5%, 20 mg/kg p.o.) | 135 ±8 | 247 ±62 | 328 ±64 | 435 ±76 | 538 ±97 | 639 ±87 | 50 |
| SEQ-ID: NO-1-ODN + tamoxifen (6 mg/kg i.v. + 20 mg/kg p.o. in NaCl 0.9% and 0.5% meth.-cellul.) | 132 ±17 | 180 ±40 | 202 ±60 | 214 ±61 | 235 ±79 | 264 ±98 | 13 |

*Complete cure in all 6 animals

Example 2: Effect of SEQ ID: NO-1-ODN in Combination with Estracyt or Cisplatin against the s.c. Transplanted Human Prostate Carcinoma PC3 in Male Balb/c Nude Mice

Example 3 Effect of SEQ ID: NO-1-ODN in Combination with Estracyt or Cisplatin against the s.c. Transplanted Human Prostate Carcinoma DU145 in Male Balb/c Nude Mice

| Treatment | day 12 | day 19 | day 22 | day 26 | day 33 | T/C % |
|---|---|---|---|---|---|---|
| Placebo treated controls (water), 25 ml/kg p.o.) | 113 ±0 | 281 ±16 | 769 ±78 | 1110 ±96 | 1525 ±160 | 100 |
| SEQ-ID: NO-1-ODN alone (NaCl 0.9%), 6 mg/kg i.v.) | 106 ±14 | 151 ±51 | 209 ±89 | 300 ±112 | 416 ±152 | 22 |
| estracyt alone (50 mg/kg i.v. in 5% mannitol) | 107 ±14 | 293 ±16 | 690 ±97 | 945 ±160 | 1230 ±189 | 80 |
| SEQ-ID: NO-1-ODN + estracyt (6 mg/kg and 50 mg/kg in NaCl 0.9% and mannitol 5%) | 113 ±0 | 158 ±47 | 225 ±93 | 266 ±100 | 336 ±125 | 16 |
| cisplatin alone (11 mg/kg i.v. in pharmacopoe) | 111 ±13 | 81 ±10 | 51 ±8 | 34 ±8 | 43 ±14 | * |
| SEQ-ID: NO-1-ODN + cisplatin (6 mg/kg i.v. and 11 mg/kg i.v. in NaCl 0.9% and pharmacopoe) | 113 ±13 | 57 ±15 | 25 ±9 | 9 ±6 | 0 ±0 | ** |

*Regression
**Complete Cure in all 6 animals

Example 3 Effect of SEQ ID: NO-1-ODN in Combination with Estracyt or Cisplatin against the s.c. Transplanted Human Prostate Carcinoma DU145 in Male Balb/c Nude Mice

| Treatment | day 9 | day 13 | day 17 | day 20 | day 23 | T/C % |
|---|---|---|---|---|---|---|
| Placebo treated controls (NaCl 0.9%, 10 ml/kg i.v.) | 116 ±15 | 451 ±85 | 852 ±138 | 1323 ±219 | 1729 ±211 | 100 |
| SEQ-ID: NO-1-ODN alone (NaCl 0.9%, 6 mg/kg i.v.) | 125 ±24 | 233 ±56 | 376 ±65 | 583 ±120 | 799 ±192 | 42 |
| estracyt alone (50 mg/kg i.v. in 5% mannitol) | 135 ±14 | 390 ±105 | 627 ±127 | 916 ±99 | 1254 ±47 | 69 |
| SEQ-ID: NO-1-ODN + estracyt (6 mg/kg and 50 mg/kg in NaCl 0.9% and mannitol 5%) | 123 ±10 | 199 ±22 | 276 ±35 | 379 ±29 | 515 ±59 | 24 |
| cisplatin alone (11 mg/kg i.v. in pharmacopoe) | 119 ±10 | 242 ±52 | 417 ±49 | 616 ±83 | 838 ±65 | 45 |
| SEQ-ID: NO-1-ODN + cisplatin (6 mg/kg i.v. and 11 mg/kg i.v. in NaCl 0.9% and pharmacopoe) | 123 ±10 | 186 ±40 | 238 ±76 | 313 ±113 | 422 ±179 | 19 |

Example 4: Effect of SEQ ID: NO-1-ODN in Combination with 5-fluorouracil or Adriamycin against the s.c. Transplanted Human Colon Carcinoma Colo 205 in Female Balb/c Nude Mice

| Treatment | day 12 | day 17 | day 20 | day 24 | day 29 | T/C % |
|---|---|---|---|---|---|---|
| Placebo treated controls (NaCl 0.9%, 10 ml/kg i.v.) | 116 ±8 | 253 ±39 | 515 ±60 | 1017 ±104 | 1711 ±213 | 100 |
| SEQ-ID: NO-1-ODN alone (NaCl 0.9%, 6 mg/kg i.v.) | 100 ±15 | 88 ±20 | 110 ±21 | 175 ±45 | 237 ±67 | 9 |
| 5-fluorouracil (75 mg/kg i.v. in NaCl 0.9%) | 113 ±13 | 131 ±26 | 142 ±31 | 149 ±37 | 157 ±43 | 3 |
| SEQ-ID: NO-1-ODN + 5-fluorouracil (6 mg/kg and 75 mg/kg in NaCl 0.9%) | 123 ±16 | 84 ±30 | 81 ±25 | 70 ±35 | 48 ±26 | –79* |
| adriamycin alone (9 mg/kg i.v. in 0.9% NaCl) | 119 ±10 | 177 ±38 | 336 ±76 | 567 ±100 | 819 ±71 | 44 |
| SEQ-ID: NO-1-ODN + adriamycin (6 mg/kg i.v. + 9 mg/kg i.v. in NaCl 0.9%) | 113 ±0 | 99 ±22 | 105 ±21 | 101 ±21 | 102 ±18 | –10 |

*regression (T/C % = –79%); strong synergism

Example 5: Effect of SEQ ID: NO-1-ODN in Combination with 5-fluorouracil or Adriamycin against the s.c. Transplanted Human Colon Carcinoma WiDr in Male Balb/c Nude Mice:

| Treatment | day 10 | day 17 | day 24 | day 28 | day 35 | T/C % |
|---|---|---|---|---|---|---|
| Placebo treated controls (NaCl 0.9%, 10 ml/kg i.v.) | 126 ±16 | 306 ±79 | 857 ±120 | 1139 ±200 | 1438 ±191 | 100 |
| SEQ-ID: NO-1-ODN alone (NaCl 0.9% 6 mg/kg i.v.) | 123 ±10 | 164 ±37 | 308 ±81 | 409 ±100 | 508 ±124 | 29 |
| 5-fluorouracil (75 mg/kg i.v. in NaCl 0.9%) | 116 ±8 | 201 ±19 | 400 ±56 | 514 ±86 | 729 ±124 | 47 |
| SEQ-ID: NO-1-ODN + 5-fluorouracil (6 mg/kg and 75 mg/kg in NaCl 0.9%) | 140 ±23 | 149 ±36 | 241 ±47 | 342 ±64 | 429 ±99 | 22 |
| adriamycin alone (9 mg/kg i.v. in 0.9% NaCl) | 119 ±10 | 225 ±39 | 550 ±93 | 821 ±134 | 1091 ±142 | 74 |
| SEQ-ID: NO-1-ODN + adriamycin (6 mg/kg i.v. + 9 mg/kg i.v. in NaCl 0.9%) | 130 ±21 | 124 ±46 | 200 ±68 | 275 ±93 | 370 ±178 | 18 |

Example 6: Effect of SEQ ID: NO-1-ODN in Combination with Mitomycin, Ifosfamide or Cisplatin against the s.c. Transplanted Human Large Cell Lung Carcinoma NCl H460 in Female Balb/C Nude Mice:

| Treatment | day 4 | day 8 | day 11 | day 14 | day 18 | day 22 | T/C % (day 18) |
|---|---|---|---|---|---|---|---|
| Placebo treated controls (NaCl 0.9%, 10 ml/kg i.v.) | 121 ±12 | 647 ±83 | 1124 ±186 | 1618 ±182 | 2229 ±232 | not done | 100 |
| SEQ-ID: NO-1-ODN alone (NaCl 0.9%, 6 mg/kg i.v.) | 126 ±16 | 226 ±69 | 345 ±139 | 550 ±230 | 862 ±316 | not done | 35 |
| mitomycin (3.5 mg/kg i.v. in NaCl 0.9%) | 107 ±14 | 85 ±14 | 65 ±0 | 65 ±0 | 70 ±7 | 54 ±14 | –47* |
| SEQ-ID: NO-1-ODN + mitomycin (6 mg/kg and 3.5 mg/kg in NaCl 0.9%) | 119 ±16 | 77 ±10 | 36 ±5 | 21 ±5 | 8 ±5 | 1 ±2 | –99** |
| ifosfamide alone (150 mg/kg i.v. in 0.9% NaCl) | 116 ±8 | 206 ±61 | 332 ±167 | 568 ±198 | 879 ±210 | not done | 36 |
| SEQ-ID: NO-1-ODN + ifosfamide (6 mg/kg i.v. + 150 mg/kg i.v./NaCl 0.9%) | 123 ±10 | 191 ±48 | 255 ±56 | 401 ±121 | 575 ±162 | 918 ±244 | 21 |

| Treatment | Tumor volume in mm³ (mean ± sem) on | | | | | | T/C % |
|---|---|---|---|---|---|---|---|
| | day 4 | day 8 | day 11 | day 14 | day 18 | day 22 | (day 18) |
| cisplatin alone (11 mg/kg i.v. in 0.9% NaCl) | 113 ±0 | 152 ±34 | 227 ±106 | 415 ±115 | 679 ±80 | 1021 ±85 | 27 |
| SEQ-ID: NO-1-ODN + cisplatin (6 mg/kg i.v. and 11 mg/kg i.v. in NaCl 0.9%) | 132 ±0 | 151 ±19 | 201 ±48 | 307 ±120 | 436 ±179 | 822 ±294 | 14 |

*regression (T/C % = −47)

**complete cure in 4 out of 6 animals after 22 days, in 5 out of 6 animals after 29 days T/C % on day 18 = −99%).

Example 7: Effect of SEQ ID: NO-1-ODN in Combination with Mitomycin, Ifosfamide or Adriamycin against the s.c. Transplanted Human Squameous Cell Lung Carcinoma NCl H520 in Female Balb/c Nude Mice:

| Treatment | Tumor volume in mm³ (mean ± sem) on | | | | T/C % |
|---|---|---|---|---|---|
| | day 8 | day 12 | day 16 | day 20 | |
| Placebo treated controls (NaCl 0.9%, 10 ml/kg i.v.) | 187 ±15 | 529 ±44 | 980 ±68 | 1739 ±115 | 100 |
| SEQ-ID: NO-1-ODN alone (NaCl 0.9%, 6 mg/kg i.v.) | 187 ±15 | 240 ±41 | 351 ±62 | 563 ±102 | 24 |
| mitomycin (3.5 mg/kg i.v. in NaCl 0.9%) | 197 ±13 | 226 ±40 | 238 ±48 | 291 ±103 | 6 |
| SEQ-ID: NO-1-ODN + mitomycin (6 mg/kg and 3.5 mg/kg in NaCl 0.9%) | 207 ±32 | 188 ±13 | 168 ±30 | 157 ±66 | * |
| ifosfamide alone (150 mg/kg i.v. in 0.9% NaCl) | 232 ±40 | 382 ±53 | 790 ±72 | 1485 ±107 | 81 |
| SEQ-ID: NO-1-ODN + ifosfamide (6 mg/kg i.v. + 150 mg/kg i.v. NaCl 0.9%) | 222 ±40 | 225 ±60 | 361 ±133 | 676 ±266 | 29 |
| adriamycin alone (9 mg/kg i.v. in 0.9% NaCl) | 193 ±14 | 317 ±52 | 586 ±83 | 990 ±78 | 51 |
| SEQ-ID: NO-1-ODN + adriamycin (6 mg/kg i.v. + 9 mg/kg i.v. in NaCl 0.9%) | 235 ±28 | 276 ±52 | 482 ±106 | 845 ±134 | 39 |

*regression in 5 out of 6 animals

Example 8: Effect of SEQ ID: NO-1-ODN in Combination with Mitomycin or Adriamycin against the s.c. Transplanted Human Melanoma SK-mel 1 in Male Balb/c Nude Mice:

| Treatment | Tumor volume in mm³ (mean ± sem) on | | | | T/C % |
|---|---|---|---|---|---|
| | day 11 | day 18 | day 25 | day 32 | |
| Placebo treated controls (NaCl 0.9%, 10 ml/kg i.v.) | 126 ±16 | 269 ±36 | 635 ±118 | 1025 ±130 | 100 |
| SEQ-ID: NO-1-ODN alone (NaCl 0.9%, 6 mg/kg i.v.) | 126 ±16 | 148 ±55 | 183 ±71 | 302 ±118 | 20 |
| mitomycin (3.5 mg/kg i.v. in NaCl 0.9%) | 113 ±0 | 115 ±26 | 119 ±16 | 125 ±20 | 1 |
| SEQ-ID: NO-1-ODN + mitomycin (6 mg/kg and 3.5 mg/kg in NaCl 0.9%) | 138 ±16 | 88 ±26 | 58 ±29 | 76 ±25 | −45* |
| adriamycin alone (9 mg/kg i.v. in 0.9% NaCl) | 123 ±10 | 181 ±43 | 241 ±48 | 518 ±150 | 44 |
| SEQ-ID: NO-1-ODN + adriamycin (6 mg/kg i.v. + 9 mg/kg i.v. in NaCl 0.9%) | 129 ±8 | 124 ±30 | 163 ±55 | 199 ±55 | 8 |

*regression (T/C % = −45)

Discussion of the Examples with Combination Studies with the SEQ-ID NO: 1-ODN and Standard Chemotherapeutic Drugs SEQ-ID NO: 1-ODN is tested at a dose of 6 mg/kg i.v. in combination with standard chemotherapeutic agents against PC3 and DU145 human prostate carcinomas, Colo 205 and WiDr human colon carcinomas, NCl-H460, NCl-H520 human lung carcinomas and SK-mel 1 human melanomas. The chemotherapeutic drugs used are adriamycin, estracyt, cisplatin, 5-fluorouracil, mitomycin, ifosfamide, vinblastine and tamoxifen which are applied according to established chemotherapeutic schedules for the respective tumor types. The SEQ-ID NO: 1-ODN exerts positive antitumor effects as combination with adriamycin, estracyt, 5-fluorouracil and ifosfamide against human prostate, colon, and melanoma tumors transplanted into nude mice. The combination of the SEQ-ID NO: 1-ODN with cisplatin in PC3 human prostate carcinomas results in a strong synergistic effect resulting in complete cures. Similarly, the combination of the SEQ-ID NO: 1-ODN and mitomycin against NCl-H460 human large cell lung carcinomas also results in a strong synergistic antitumor effect with complete cures. In other lung carcinomas, positive effects with mitomycin or cis-platin and the SEQ-ID NO: 1-ODN are found. In human breast carcinoma MCF-7 treatment, the combination the SEQ-ID NO: 1-ODN with vinblastine leads to complete cure in all test animals. Most importantly, in no case antagonistic influences between the SEQ-ID NO: 1-ODN and chemotherapeutic agents or increased overt toxicity are observed. These results indicate that the SEQ-ID NO: 1-ODN exerts beneficial antitumor effects both as a single agents and in an improved manner in combination with chemotherapeutic drugs in the treatment of human cancer.

What is claimed is:

1. A method for treating cancer in a mammal comprising administering to said mammal:

(a) an antisense oligonuclotide targeted to PKC consisting of 10–35 nucleotides comprising the following nucleic acid sequence:

5'-GTT CTC GCT GGT GAG TTT CA-3'    SEQ ID NO:1, or a sequence that differs from said sequence by up to 3 nucleotides, or a derivative of said oligonucleotide, and (b) a chemotherapeutic agent or combination thereof selected from the following:
(i) vinblastine,
(ii) cisplatin,
(iii) 5-fluorouracil,
(iv) mitomycin,
(v) adriamycine
(vi) vinblastine and adriamycine, or
(vii) 5-fluorouracil and adriamycine;

wherein component (a) and/or (b) can be present in the form of a pharmaceutically acceptable salt, if at least one salt-forming group is present, and wherein the combination of (a) and (b) has a synergistic anti-tumor effect.

2. The method of claim 1 according to one of the following:

(i) wherein said cancer is breast cancer and said chemotherapeutic agent is vinblastine and/or adriamycine (ii) wherein said cancer is prostate carcinoma and said chemotherapeutic agent is cisplatin (iii) wherein said cancer is colon carcinoma and said chemotherapeutic agent is 5-fluorouracil and/or adriamycine (v) wherein said cancer is lung carcinoma and said chemotherapeutic agent is mitomycin.

3. The method according to claim 2 wherein (a) comprises at least one of the following base-sugar or base-sugar analogue units of the formulae given hereinafter, wherein B is a base radical of a base selected from thymine, uracil, 5-propynyluracil, cytosine, 5-methylcytosine, 5-propynylcytosine, adenine, 2-aminoadenine or guanine; Q is H, $OCH_3$, F, $O(CH_2CH_2O)_vCH_3$ wherein v is from 0–12, $CH_2CH(CH_3)OCH_3$ or $CH_2CH(OH)CH_2OH$; and the other moieties have the standard meanings given behind the formula:

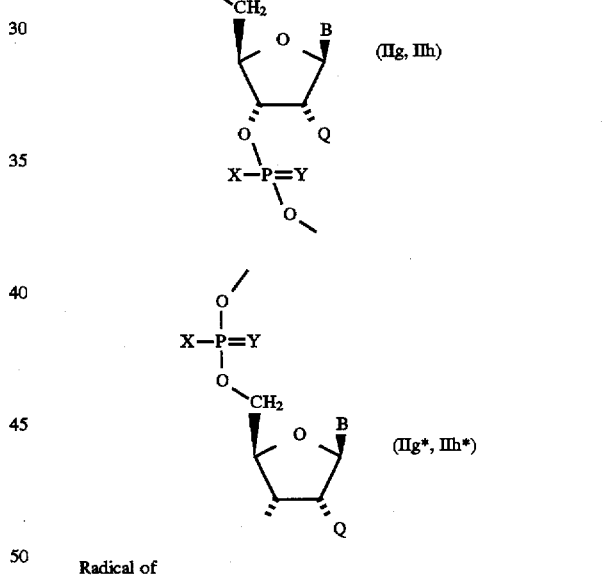

| Radical of formula | type | | |
|---|---|---|---|
| (IIg), (IIg*) | phosphorothioate | X = SH | Y = O or S |
| (IIh) (IIh*) | phosphodiester | X = OH | Y = O | the remaining internucleosidic bonds in the oligonucleotide derivative being of the phosphorothioate type; or wherein (a) comprises at least one of the following dimeric units of the formulae given hereinafter, wherein each B is, independently of the other, a base radical selected from thymine, uracil, 5-propynyluracil, cytosine, 5-methylcytosine, 5-propynylcytosine, adenine, 2-aminoadenine and guanine; each Q is, independently of the other, H, $OCH_3$, F or $O(CH_2CH_2O)_v$, wherein v is from 0 to 12; and the other moieties have the standard meanings given behind the formula:

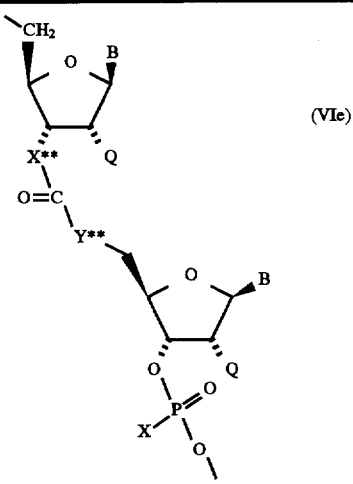

| Radical of formula | type | X | Y |
|---|---|---|---|
| (VIe), (VIe*) | amide | CH₂ | N(A) | wherein A is H, methyl or phenyl, and the remaining internucleosidic bonds in the oligonucleotide derivative are of the phosphorothioate type, wherein A is H, methyl or phenyl, and the remaining internucleosidic bonds in the oligonucleotide derivative are of the phosphorothioate type.

4. The method according to claim 2 wherein (a) is a phosphorothioate oligo-2'-dexoynucleotide analogue of SEQ ID NO: 1, or a derivative thereof with 15 to 19 base-sugar analogue units of the phosphorothioate 2'-deoxynucleotide type, or a pharmaceutically acceptable salt thereof.

5. The method according to claim 2 wherein (a) is a phosphorothioate oligo-2'-dexoynucleotide analogue of SEQ ID NO: 1, or a pharmaceutically acceptable salt thereof.

6. The method according to claim 5 wherein (a) and (b) are administered to a mammal in combination in a quantity which is jointly therapeutically active against the cancer being treated, and wherein (a) and/or (b) can be present in the form of a pharmaceutically acceptable salt, if at least one salt-forming group is present.

7. A pharmaceutical preparation for the treatment of cancer in a mammal comprising:

(a) an antisense oligonuclotide targeted to PKC consisting of 10–35 nucleotides comprising the following nucleic acid sequence:

5'-GTT CTC GCT GGT GAG TTT CA-3'    SEQ ID NO:1, or a sequence that differs from said sequence by up to 3 nucleotides, or a derivative of said oligonucleotide, and (b) a chemotherapeutic agent or combination thereof selected from the following:
(i) vinblastine,
(ii) cisplatin,
(iii) 5-fluorouracil,
(iv) mitomycin,
(v) adriamycine
(vi) vinblastine and adriamycine, or
(vii) 5-fluorouracil and adriamycine; and one or more pharmaceutically acceptable carrier materials, wherein component (a) and/or (b) can be present in the form of a pharmaceutically acceptable salt, if at least one salt-forming group is present, and wherein the combination of (a) and (b) has a synergistic anti-tumor effect.

8. The pharmaceutical preparation of claim 7 according to one of the following:

(i) wherein said cancer is breast cancer and said chemotherapeutic agent is vinblastine and/or adriamycine (ii) wherein said cancer is prostate carcinoma and said chemotherapeutic agent is cisplatin (iii) wherein said cancer is colon carcinoma and said chemotherapeutic agent is 5-fluorouracil and/or adriamycine (iv) wherein said cancer is lung carcinoma and said chemotherapeutic agent is mitomycin.

9. The pharmaceutical preparation according to claim 8 wherein (a) comprises at least one of the following base-sugar or base-sugar analogue units of the formulae given hereinafter, wherein B is a base radical of a base selected from thymine, uracil, 5-propynyluracil, cytosine, 5-methylcytosine, 5-propynylcytosine, adenine, 2-aminoadenine or guanine; Q is H, OCH₃, F, O(CH₂CH₂O)ᵥCH₃ wherein v is from 0–12, CH₂CH(CH₃)OCH₃ or CH₂CH(OH)CH₂OH; and the other moieties have the standard meanings given behind the formula:

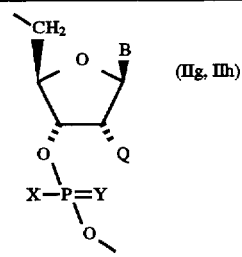

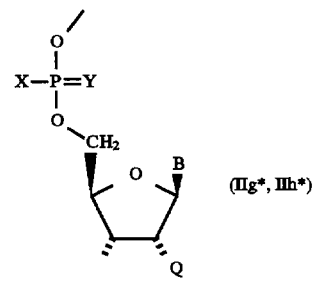

| Radical of formula | type | | |
|---|---|---|---|
| (IIg), (IIg*) | phosphorothioate | X = SH | Y = O or S |
| (IIh), (IIh*) | phosphodiester | X = OH | Y = O | the remaining internucleosidic bonds in the oligonucleotide derivative being of the phosphorothioate type; or wherein (a) comprises at least one of the following dimeric units of the formulae given hereinafter, wherein each B is, independently of the other, a base radical selected from thymine, uracil, 5-propynyluracil, cytosine, 5-methylcytosine, 5-propynylcytosine, adenine, 2-aminoadenine and guanine; each Q is, independently of the other, H, OCH₃, F or O(CH₂CH₂O)ᵥ wherein v is from 0 to 12; and the other moieties have the standard meanings given behind the respective formula:

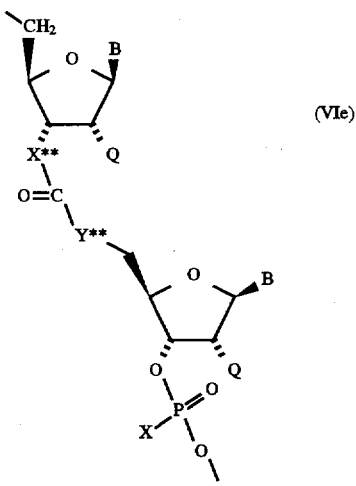

| Radical of formula | type | X | Y |
|---|---|---|---|
| (VIe), (VIe*) | amide | $CH_2$ | N(A) | wherein A is H, methyl or phenyl, and the remaining internucleosidic bonds in the oligonucleotide derivative are of the phosphorothioate type.

wherein A is H, methyl or phenyl, and the remaining internucleosidic bonds in the olignucleotide derivative are of the phosphorothioate type.

10. The pharmaceutical preparation according to claim 8 wherein (a) is a phosphorothioate oligo-2'-dexoynucleotide analogue of SEQ ID NO: 1 or a derivative thereof with 15 to 19 base-sugar analogue units of the phosphorothioate 2'-deoxynucleotide type, or a pharmaceutically acceptable salt thereof.

11. The pharmaceutical preparation according to claim 8 wherein (a) is a phosphorothioate oligo-2'-dexoynucleotide analogue of SEQ ID NO: 1, or a pharmaceutically acceptable salt thereof.

12. The pharmaceutical preparation according to claim 8 wherein (a) and (b) are administered to a mammal in combination in a quantity which is jointly therapeutically active against the cancer being treated, and wherein (a) and/or (b) can be present in the form of a pharmaceutically acceptable salt, if at least one salt-forming group is present.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="antisense oligonucleotide"

( i v ) ANTI-SENSE: YES ( x i ) SEQUENCE DESCRIPTION: SEQ ID NO: 1:

GTTCTCGCTG GTGAGTTTCA 20